United States Patent
Arimura

(10) Patent No.: US 6,506,789 B2
(45) Date of Patent: Jan. 14, 2003

(54) METHODS FOR THE TREATMENT OF ITCHING COMPRISING ADMINISTERING PGD2 RECEPTOR ANTAGONIST

(75) Inventor: Akinori Arimura, Toyonaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 09/881,799

(22) Filed: Jun. 18, 2001

(65) Prior Publication Data

US 2002/0058693 A1 May 16, 2002

Related U.S. Application Data

(63) Continuation of application No. 09/700,283, filed as application No. PCT/JP99/02820 on May 28, 1999.

(30) Foreign Application Priority Data

Jun. 3, 1998 (JP) .......................................... 10-154332

(51) Int. Cl.$^7$ .................. A61K 31/38; A61K 31/34; A61K 31/24; A61K 31/195
(52) U.S. Cl. .................. 514/443; 514/445; 514/448; 514/468; 514/469; 514/538; 514/562
(58) Field of Search ................ 514/443, 445, 514/448, 468, 469, 538, 562

(56) References Cited

U.S. PATENT DOCUMENTS

| | | |
|---|---|---|
| 4,792,550 A | 12/1988 | Miyake et al. |
| 4,904,819 A | 2/1990 | Hagishita et al. |
| 4,923,875 A | 5/1990 | Frost |
| 5,168,101 A | 12/1992 | Arai et al. |
| 6,172,113 B1 * | 1/2001 | Ohtani et al. ............... 514/562 |

FOREIGN PATENT DOCUMENTS

| | | |
|---|---|---|
| EP | 0 837 052 A1 | 4/1998 |
| JP | 3 204815 A | 6/1991 |
| WO | 97/00853 A1 | 9/1997 |
| WO | 97/44031 | 11/1997 |

OTHER PUBLICATIONS

Musoh et al., "Scratching behavior in mice associated with IgE–mediated allergic cutaneous reaction and its pharmacological characterization," *Allergology Int.*, 46:117–124 (1997), Japanese Society of Allergology.

*Nippon Kagaku Zasshi*, 88(7):758–763 (1967), Chemical Society of Japan.

*Nippon Kagaju Zasshi*, 86(10):1067–1072 (1965), Chemical Society of Japan.

Martin–Smith and Sneader, "Beno[β]thiophen Derivatives. Part VI. The Synthesis of 3–(2–Amino–ethyl)–5–hydroxybenzo[β]thiophen and Related Compounds," *J. Chem. Soc.*, (C) pp. 1899–1905 (1967), Royal Society of Chemistry.

Titus and Titus, "2–Amino–3–(6–methoxybenzo[β] thien–3–yl)propanoic Acid (1),".

J. Heterocycle, Chem., 10:679–681 (1973), Hetero Corporation.

Hannoun et al., "*alpha*–Phenypropionic Acid Derivatives Synthesis and Dethiation of 5–Benzoylbenzo[β] thiophene–3–carboxylic Acid," *J. Heterocyclic. Chem.*, 19:1131–1136 (1982), Hetero Corporation.

Cross et al., "Selective Thromboxane Synthetase Inhibitors. 3. 1*H*–Imidazol–1–yl–Substituted Benzo[β]furan–, Benzo[β] thiophene–, and Indole–2– and —3 carboxylic Acids," *J. Med. Chem.*, 29:1637–1643 (1986) The American Chemical Society.

*Shin–Jikken–Kagaku–Koza*, vol. 14, 1787 (1978), Chemical Society of Japan.

Hamada and Yonemitsu, "An Improved Synthesis of Arylsulfonyl Chlorides from Aryl Halides," *Synthesis* pp. 852–854 (1986), Georg Thieme Verlag.

*Shin–Jikken–Kagaku–Koza*, vol. 22, 115 (1992), Chemical Society of Japan.

Seno and Hagishita, "Thromboxane $A_2$ Receptor Antagonists. III. Synthesis and Pharmacological Activity of 6,6–Dimethylbicyclo[3. 1. 1]heptane Derivatives with a Substituted Sulfonylamino Group at C–2," *Chem. Pharm. Bull.*, 37(6):1524–1533 (1989), Pharmaceutical Society of Japan.

D.F. Woodward, et al., "Characterization of Receptor Subtypes Involved in Prostanoid–Induced Conjunctival", The Journal of Pharmacology and Experimental Therapeutics, vol. 279, No. 1, , pp. 137–142 (1996).

* cited by examiner

*Primary Examiner*—Zohreh Fay
*Assistant Examiner*—Brian-Yong S. Kwon
(74) *Attorney, Agent, or Firm*—Foley & Lardner

(57) ABSTRACT

A $PGD_2$ receptor antagonist such as a compound of the formula (IA-a-5):

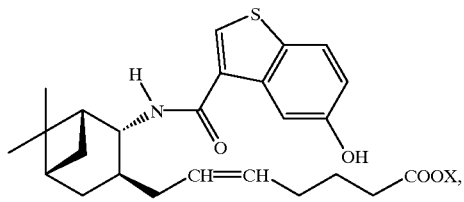

IA-a-5 a pharmaceutical acceptable salt thereof or a hydrate thereof, has an efficacious activity for the prevention or treatment of itching and is useful as a medicament.

8 Claims, No Drawings

METHODS FOR THE TREATMENT OF ITCHING COMPRISING ADMINISTERING PGD2 RECEPTOR ANTAGONIST

This application is a continuation of application Ser. No. 09/700,283 filed Nov. 13, 2000, which is a 371 of PCT/JP99/02820, filed May 28, 1999.

TECHNICAL FIELD

The present invention relates to a pharmaceutical composition for the prevention or treatment of itching comprising a prostaglandin $D_2$ ($PGD_2$) receptor antagonist.

BACKGROUND ART $PGD_2$ is a major prostanoid released from mast cells in which it is produced through $PGG_2$ and $PGH_2$ from arachidonic acid by the action of cyclooxygenase activated by immunological or unimmunological stimulation. $PGD_2$ has been known to cause allergic disorders such as allergic rhinitis and allergic conjunctivitis because it shows various physiological effects such as induction of nasal obstruction, vasodilator effect, wandering of eosinophils and the like. Accordingly, $PGD_2$ receptor antagonists have been thought to be useful for the treatment thereof (WO97/00853).

Moreover, a large quantity of $PGD_2$ is also released from macrophages, so $PGD_2$ may play a role in causing an inflammatory response independent of allergy.

On the other hand, itching has been known to be accompanied by diseases such as atopic dermatitis, urticaria, allergic rhinitis, allergic conjunctivitis and the like as well as inflammatory responses such as swelling and the like. Moreover, the action accompanied by itching, for example scratching, knocking and the like may worsen the condition of the above-mentioned diseases. Therefore, the development of a compound for the treatment of itching has been desired, which is further expected to be a pharmaceutical composition for the prevention or treatment of diseases secondarily caused by the action against itching, for example cararacta, retinal detachment, inflammation, infection, dysgryphia and the like.

At present, antihistaminic agents are used as therapeutic agents for itching. They show an effect on swelling, but the effect against itching is by no means sufficient. Thus, it is suggested in Allergology Int., 1997, 46, 117–124 that itching may be caused by a mediator other than histamine.

A $PGD_2$ receptor antagonist used in the present invention has been known to be useful for the treatment of allergic condition caused by $PGD_2$ such as rhinitis and the like (WO97/00853). Any positive data concerning the prevention or treatment of itching has not been described.

On the other hand, it is described in J. Pharmacol. Exp. Ther., 279, 137–142, 1996 that instillation of $PGD_2$ in guinea pig induces itching, which is inhibited by a $PGD_2$ receptor antagonist, BWA868C. But it is not described that a $PGD_2$ receptor antagonist is useful for the treatment of itching caused by allergy. Further described is that a $PGD_2$ receptor antagonist, BWA868C, can not inhibit itching caused by antigens at all, which is similar to disease models.

On the other hand, it is described that Ramatroban, inhibiting the contraction of smooth muscle of bronchus caused by $TXA_2$ or $PGD_2$ stimulation, is efficacious against contact dermatitis or atopic dermatitis mediated by delayed allergy (WO97/44031). However, Ramatroban described in said specification is a $TXA_2$ receptor antagonist, but not a $PGD_2$ receptor antagonist. Moreover, the therapeutic effect of Ramatroban against atopic dermatitis is based on the suppression of swelling caused by the delayed-type allergy reaction. Thus, the suppression effect against itching is not described. Therefore, it is not suggested that a $PGD_2$ receptor antagonist of the present invention suppresses itching and useful for the treatment of atopic dermatitis.

DISCLOSURE OF INVENTION $PGD_2$, a mediator mass-produced through allergy reaction, is supposed to play an important role as a mediator in itching. Indeed, we have discovered through an experiment using mice that a $PGD_2$ receptor antagonist is efficacious against itching to accomplish the present invention. Therefore, the present invention provides a composition for the prevention or treatment of itching comprising a $PGD_2$ receptor antagonist. In detail, the present invention provides a composition for the prevention or treatment of itching caused by an antigen, especially a composition for the treatment of itching derived from atopic dermatitis, urticaria, allergic conjunctivitis, allergic rhinitis or contact dermatitis.

A $PGD_2$ receptor antagonist used in the present invention has an activity of preventing or treating itching and so it is able to be used for a pharmaceutical composition for the prevention or treatment of itching. The term "itching" to be used in the present specification means itching caused by an allergic reaction or a non-allergic reaction.

The allergic reaction means reactions caused by the activation of mast cell, basophil and the like due to the reaction of an antigen with the antigen-specific IgE and the delayed-type allergy reaction such as contact dermatitis. The non-allergic reaction means a reaction which is independent of IgE and caused by mast cells, basophils and the like activated by a chemical substance or the like.

The $PGD_2$ receptor antagonist suppresses itching derived from the allergic reaction or non-allergic reaction and is useful for the prevention or treatment of the accompanying inflammation such as atopic dermatitis, urticaria, allergic conjunctivitis, allergic rhinitis, contact dermatitis and the like.

Moreover, the $PGD_2$ receptor antagonist is useful for the prevention or treatment of a secondary disease such as cararacta, retinal separation, inflammation, infection, dysgryphia or the like, which is caused by an action accompanied by itching, for example, scratching, knocking and the like.

BEST MODE FOR CARRYING OUT THE INVENTION

The $PGD_2$ receptor antagonist used in the present invention has an activity of preventing or treating itching. Among them, preferred is a composition for the prevention or treatment of itching comprising a compound of the following formula (I).

In a preferred embodiment, the $PGD_2$ receptor antagonist includes a compound of the formula (I):

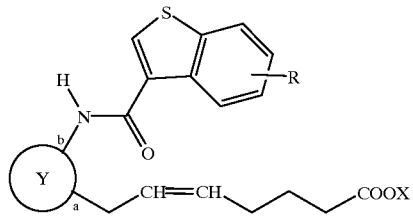

(I)

wherein

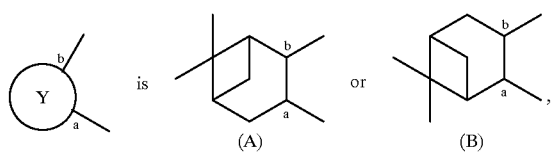

R is hydrogen, alkyl, alkoxy, halogen, hydroxy, acyloxy or optionally substituted arylsulfonyloxy, X is hydrogen or alkyl and the double bond on the α chain has E configuration or Z configuration, a pharmaceutically acceptable salt thereof or a hydrate thereof.

Through the present specification, the group of the formula in the compound of the formula (I):

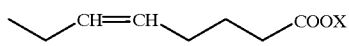

wherein X is as defined above,
is referred to as α chain and the group of the formula:

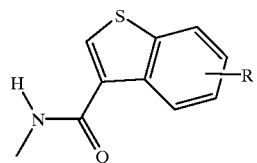

wherein R is as defined above,
is referred to as ω chain.

The double bond on the α chain has E configuration or Z configuration.

In detail, examples of the above compound include a compound of the formula (IA):

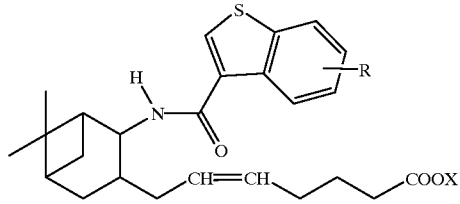

(IA)

wherein R and X are as defined above and the double bond on the α chain has E configuration or Z configuration, and a compound of the formula (IB):

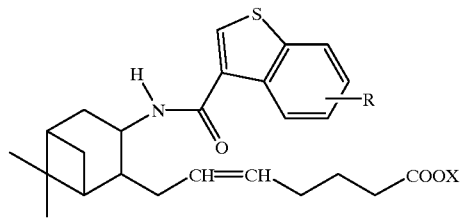

(IB)

wherein R and X are as defined above and the double bond on the α chain has E configuration or Z configuration.

In more detail, the compound of the formula (IA) includes a compound of the formula:

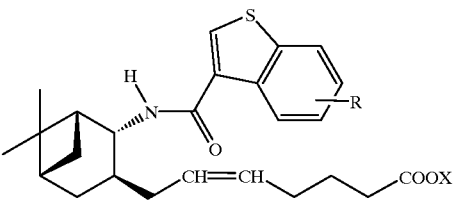

(IA-a)

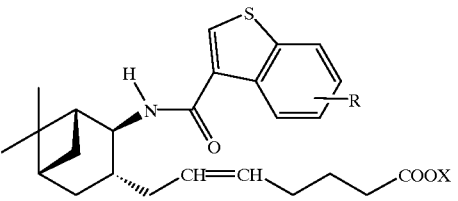

(IA-b)

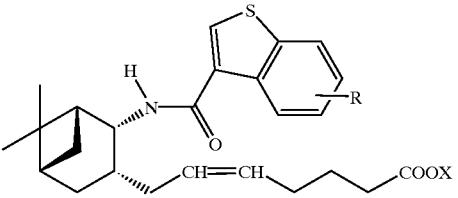

(IA-c)

(IA-d)

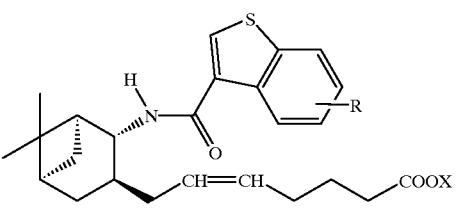

(IA-a′)

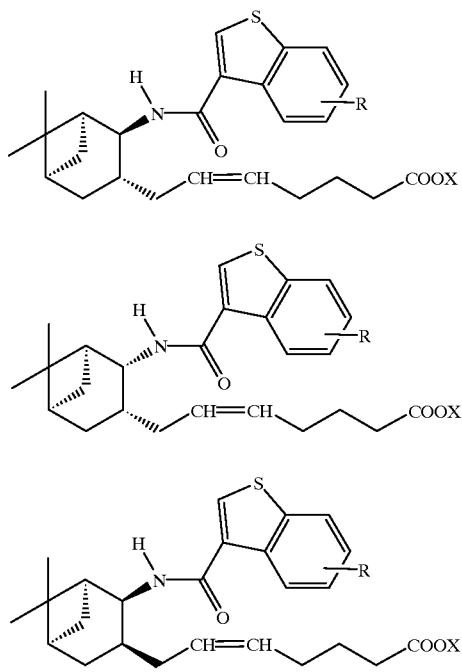

wherein R and X are as defined above and the double bond on the α chain has E configuration or Z configuration.

Preferred is the compound of the formula (IA-a), (IA-b), (IA-c), (IA-d) or (IA-b'). Especially preferred is the compound of the formula (IA-a).

The compound of the formula (IB) includes a compound of the formula:

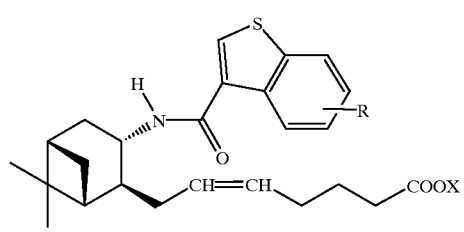

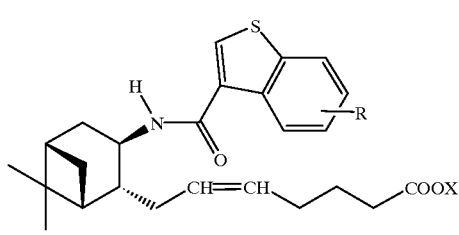

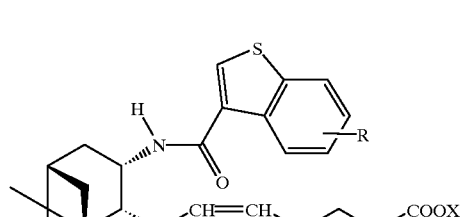

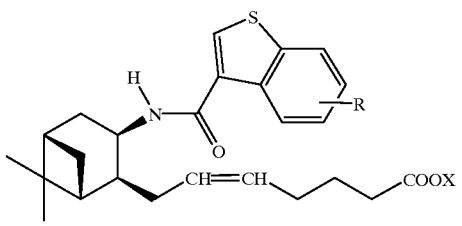

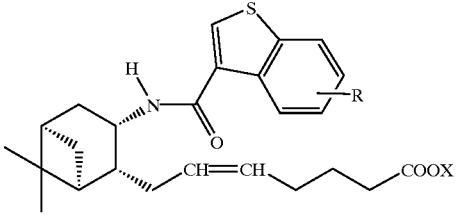

wherein R and X are as defined above and the double bond on the α chain has E configuration or Z configuration.

Preferred is the compound of the formula (IB-a') or (IB-b').

Among the above examples, preferred is a compound wherein the double bond on the α chain has E configuration, a compound wherein the double bond on the α chain has Z configuration, a compound wherein R is hydrogen, methyl, methoxy, bromo, fluoro, hydroxy, acetoxy or phenylsulfonyloxy and X is hydrogen or a compound wherein R is hydroxy and X is hydrogen.

Preferred is a compound of the formula (IA-a-5):

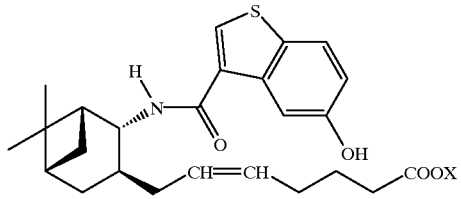

IA-a-5

A preferred PGD$_2$ receptor antagonist has a high PGD$_2$ antagonistic activity and a high selectivity. Another preferred has a low agonistic activity. For example, a preferred antagonist has a PGD$_2$ binding inhibitory activity (IC$_{50}$ value) of 1000 nM or less, 100 nM or less or especially 10 nM or less. The PGD$_2$ binding inhibitory activity (IC$_{50}$ value) can be calculated in accordance with the experiment 1 of the present specification.

Each term used in the present specification is defined below.

The term "alkyl" means C1–C6 straight or branched alkyl, for example, methyl, ethyl, n-propyl, i-propyl, n-butyl, i-butyl, s-butyl, t-butyl, n-pentyl, i-pentyl, neopentyl, t-pentyl, t-pentyl, hexyl and the like.

The term "alkoxy" means C1–C6 straight or branched alkoxy, for example, methoxy, ethoxy, n-propoxy, i-propoxy, n-butoxy and the like.

The term "halogen" is fluoro, chloro, bromo or iodo.

The term "acyl" of the term "acyloxy" means C1–C9 acyl derived from aliphatic carboxylic acid, for example, formyl, acetyl, propionyl, butyryl, valeryl and the like.

The term "acyloxy" means acyloxy derived from the above "acyl", for example, acetoxy, propionyloxy, butyryloxy, valeryloxy and the like.

The term "aryl" means C6–C14 aromatic monocyclic group or aromatic condensed ring, for example, phenyl, naphthyl (e.g., 1-naphthyl or 2-naphthyl), anthryl (e.g., 1-anthryl, 2-anthryl or 9-anthryl) and the like.

The term "arylsulfonyloxy" means arylsulfonyloxy derived from "aryl", for example, arylsulfonyloxy, 1-nathylsulfonyloxy, 1-anthrylsulfonyloxy and the like. The substituent of "aryl" includes alkyl, alkoxy, halogen, hydroxy and the like.

Examples of salts of the compound of the formula (I) includes those formed with an alkali metal (e.g., lithium, sodium or potassium), an alkali earth metal (e.g., calcium), an organic base (e.g., tromethamine, trimethylamine, triethylamine, 2-aminobutane, t-butylamine, diisopropylethylamine, n-butylmethylamine, cyclohexylamine, dicyclohexylamine, N-isopropylcyclohexylamine, furfurylamine, benzylamine, methylbenzylamine, dibenzylamine, N,N-dimethylbenzylamine, 2-chlorobenzylamine, 4-methoxybenzylamine, 1-naphthalenemethylamine, diphenylbenzylamine, triphenylamine, 1-naphthylamine, 1-aminoanthracene, 2-aminoanthracene, dehydroabiethylamine, N-methylmorpholine or pyridine), an amino acid (e.g., lysine or arginine) and the like. These salts can be formed in accordance with the general method.

The hydrates of the compound of the formula (I) may be coordinated with water molecules in an optional proportion.

The compound of the formula (I) may have all the possible stereo configurations, that is, the double bond on the α chain has E configuration or Z configuration and the bond binding to the bicyclic ring is of R configuration or S configuration, including all the stereo isomers (diastereomers, epimers, enantiomers and the like), racemates and mixtures thereof.

General processes for the preparation of the compound of the formula (I) are illustrated as follows. Any substituent interfering with a reaction may be protected in advance with a protecting group and deprotected in a suitable step.

Process 1

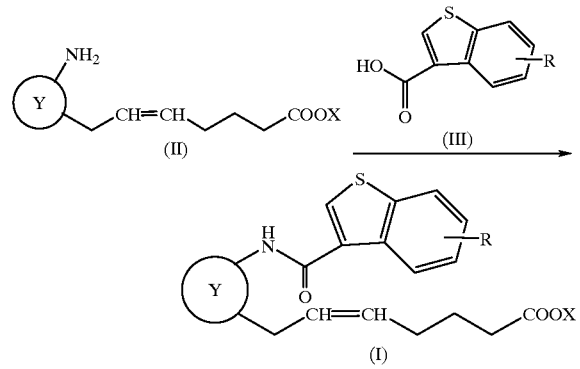

wherein Y ring, X and R are as defined above and the double bond on the α chain has E configuration or Z configuration.

The compound of the formula (I) as shown in the above process 1 can be prepared by reacting the carboxylic acid of the formula (III) or the reactive derivative with an amino compound of the formula (II).

In this process, a starting compound (II) wherein

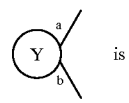

is

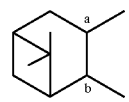

(A)

is described in the Japanese Patent Publication (Kokoku) No. 23170/1994. A compound (II) wherein

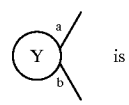

is

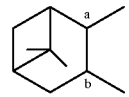

(B)

is described in the Japanese Patent Publication (Kokai) Nos. 49/1986 and 180862/1990.

The carboxylic acid of the formula (III) includes
4-bromobenzo[b]thiophene-3-carboxylic acid,
5-bromobenzo[b]thiophene-3-carboxylic acid,
6-bromobenzo[b]thiophene-3-carboxylic acid,
7-bromobenzo[b]thiophene-3-carboxylic acid,
5-fluorobenzo[b]thiophene-3-carboxylic acid,
6-fluorobenzo[b]thiophene-3-carboxylic acid,
4-hydroxybenzo[b]thiophene-3-carboxylic acid,
5-hydroxybenzo[b]thiophene-3-carboxylic acid, 6-hydroxybenzo[b]thiophene-3-carboxylic acid, 7-hydroxybenzo[b]thiophene-3-carboxylic acid, 5-acetoxybenzo[b]thiophene-3-carboxylic acid, benzo[b]thiophene-3-carboxylic acid, 5-benzosulfonyloxybenzo[b]thiophene-3-carboxylic acid, 5-methylbenzo[b]thiophene-3-carboxylic acid, 6-methylbenzo[b]thiophene-3-carboxylic acid, 5-methoxybenzo[b]thiophene-3-carboxylic acid and 6-methoxybenzo[b]thiophene-3-carboxylic acid. These carboxylic acids may have the substituents as defined above.

These carboxylic acids can be prepared in accordance with methods as described in Nippon Kagaku Zasshi Vo.188, No. 7, 758–763 (1967), Nippon Kagaku Zasshi Vol. 86, No. 10, 1067–1072 (1965), J. Chem. Soc (c) 1899–1905 (1967), J. Heterocycle. Chem. Vol. 10 679–681 (1973), J. Heterocyclic Chem. Vol 19 1131–1136 (1982) and J. Med. Chem. Vol. 29 1637–1643 (1986).

The reactive derivative of carboxylic acid of the formula (III) means the corresponding acid halide (e.g., chloride, bromide, iodide), acid anhydride (e.g., mixed acid anhydride with formic acid or acetic acid), active ester (e.g., succinimide ester) and the like, including acylating agents used for the acylation of amino group. For example, when an acid halide is employed, the compound (III) is reacted with a thionyl halide (e.g., thionyl chloride), phosphorous halide (e.g., phosphorous trichloride, phosphorous pentachloride), oxalyl halide (e.g., oxalyl chloride) and the like, in accordance with known methods as described in the literatures (e.g., Shin-Jikken-Kagaku-Koza, Vol. 14, 1787 (1978); Synthesis 852–854 (1986); Shin-Jikken-Kagaku-Koza Vol. 22, 115 (1992)).

The reaction of Process 1 can be conducted under a condition generally used for the acylation of amino group. For example, in a case of condensation with the acid halide, the reaction is carried out in a solvent such as an ether solvent (e.g., diethyl ether, tetrahydrofuran, dioxane), benzene solvent (e.g., benzene, toluene, xylene), halogenated hydrocarbon solvent (e.g., dichloromethane, dichloroethane, chloroform) as well as ethyl acetate, dimethylformamide, dimethyl sulfoxide and acetonitrile, if necessary, in the presence of a base (e.g. organic base such as triethylamine, pyridine, N,N-dimethylaminopyridine and N-methylmorpholine; inorganic base such as sodium hydroxide, potassium hydroxide and potassium carbonate. The reaction temperature is under cooling, at room temperature or under heating, preferably at a temperature ranging from −20° C. to ice-cooling temperature or from room temperature to a refluxing temperature of the reaction system. The reaction time is several minutes to several ten hours, preferably 0.5 hr to 24 hr and particularly 1 hr to 12 hr. In a case of using the carboxylic acid in a free form without converting into the reactive derivative, the reaction is conducted in the presence of a condensing agent (e.g., dicyclohexylcarbodiimide (DCC), 1-ethyl-3-(3-methylaminopropyl)carbodiimide, N,N'-carbonyldiimidazole) usually used in the condensation reaction of amine with carboxylic acid.

The compound (I) of the present invention can be also prepared in accordance with a method as follows.

Process 2

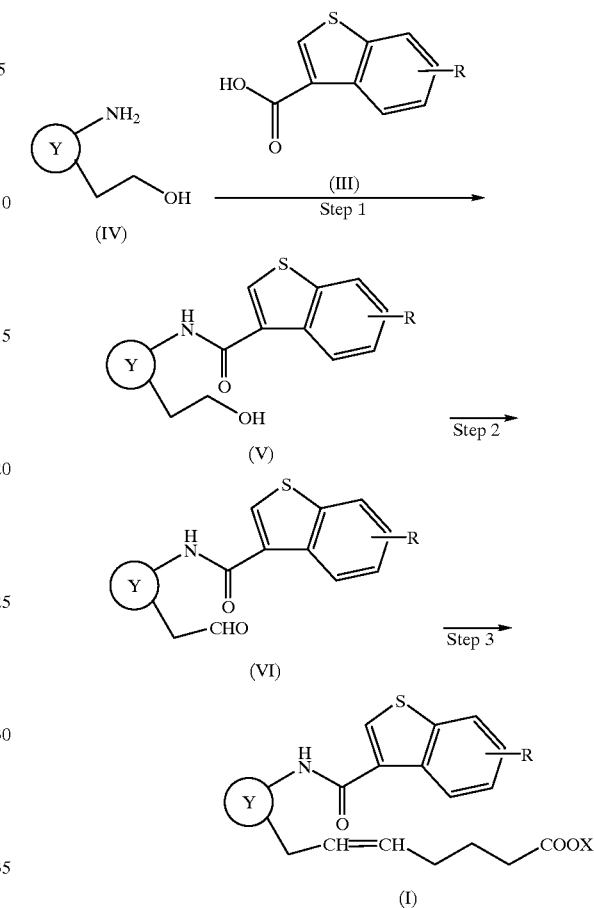

wherein Y ring, R and X are as defined above and the double bond on the α-chain has E configuration or Z configuration.

(Step 1)

In this step, the compound of the formula (V) can be prepared by reacting the amino compound of the formula (IV) with a carboxylic acid of the formula (III) or its reactive derivative, in accordance with Process 1. As to some of the amino compounds of the formula (IV), the process is disclosed in Chem. Pharm. Bull. Vol. 37, No. 6, 1524–1533 (1989).

(Step 2)

In this step, a compound of the formula (V) is oxidized to give an aldehyde compound of the formula (VI). This step may be carried out with chromated oxidizing agents such as Jones' reagent, Collins' reagent, pyridinium chlorochromate and pyridinium dichromate, in a solvent such as chlorinated hydrocarbon (e.g., chloroform, dichloromethane), ether (e.g., ethyl ether, tetrahydrofuran), acetone, benzene and the like, under cooling or at room temperature for several hours. This step may be also carried out with oxidizing agents in combination with appropriate activator agents (e.g., trifluoroacetic anhydride, oxalyl chloride) and dimethyl sulfoxide, if necessary, in the presence of base (e.g. organic base such as triethylamine, diethylamine).

(Step 3)

In this step, the α chain of an aldehyde compound of the formula (VI) is formed to give the compound of the formula (I). The compound of the formula (I) can be prepared by reacting the aldehyde compound of the formula (VI) with an ylide compound corresponding to the rest part of the α chain in accordance with conditions of the Wittig reaction. Further, the ylide compound corresponding to the rest part of the α chain can be synthesized by reacting triphenylphosphine with a corresponding halogenated alkanoic acid or ester derivative thereof in the presence of a base according to a well known method.

In a reaction of the other free acid or the reactive derivative with the amine (II) or (IV), depending on the property of each free acid or the reactive derivative, the reaction conditions are determined in accordance with a known method. The reaction product can be purified by a conventional method, such as extraction with a solvent, chromatography, recrystallization and the like.

The objective compound (I) in the present invention can be converted into a corresponding ester derivative, if desired. For example, the ester can be prepared by esterification of a carboxylic acid in accordance with a known method. If desired, E isomer, Z isomer or the mixture can be produced depending on the reaction conditions.

When using a PGD$_2$ antagonist of the present invention for treatment, it can be formulated into ordinary formulations for oral and parenteral administration. A pharmaceutical composition containing a PGD$_2$ antagonist of the present invention can be in the form for oral and parenteral administration. Specifically, the oral formulation includes tablets, capsules, granules, powders, syrup and the like. The parenteral formulation includes injectable solutions or suspensions for intravenous, intramuscular or subcutaneous injection, inhalants, eye drops, nasal drops, suppositories or percutaneous formulations such as ointment, patches and poultices. Preferred is an oral or percutaneous formulation.

In preparing the formulations, carriers, excipients, solvents and bases known to presons ordinary skilled in the art may be used. Tablets are prepared by compressing or fomulating an active ingredient together with auxiliary components. Examples of the auxiliary components include pharmaceutically acceptable excipients such as binders (e.g., cornstarch), fillers (e.g., lactose, microcrystalline cellulose), disintegrants (e.g., starch sodium glycolate) and lubricants (e.g., magnesium stearate). Tablets may be coated appropriately. In the case of liquid formulations such as syrups, solutions or suspensions, they may contain suspending agents (e.g., methyl cellulose), emulsifiers (e.g., lecithin), preservatives and the like. Injectable formulations may be in the form of solution or suspension or oily or aqueous emulsion, which may contain a suspension-stabilizing agent or dispensing agent and the like. Percutaneous formulations such as ointment, patches, poultices and the like may be prepared by using water base (e.g., water, lower alcohol, polyol) or oil base (higher fatty acid ester (isopropyl myristate), lipophilic alochol).

An appropriate dosage of PGD$_2$ receptor antagonist, depending on the administration route, age, body weight, sex or conditions of the patient and the kind of optionally combined drug(s), should be determined by a physician. In the case of oral administration, the daily dosage can generally be between about 0.01–100 mg, preferably about 0.01–10 mg, more preferably about 0.01–1 mg, per kg body weight. In the case of parenteral administration, the daily dosage can generally be between about 0.001–100 mg, preferably about 0.001–1 mg, more preferably about 0.001–0. 1 mg, per kg body weight. The daily dosage can be administered in 1–4 divisions.

The following Examples are provided to further illustrate the present invention and are not to be construed as limiting the scope.

The abbreviations used throughout the examples are shown as follows.

Me methyl

Ac acetyl

Ph phenyl

REFERENCE 1

Preparation of 5-Benzenesulfonyloxybenzo[b] thiophene-3-carbonyl Chloride (3)

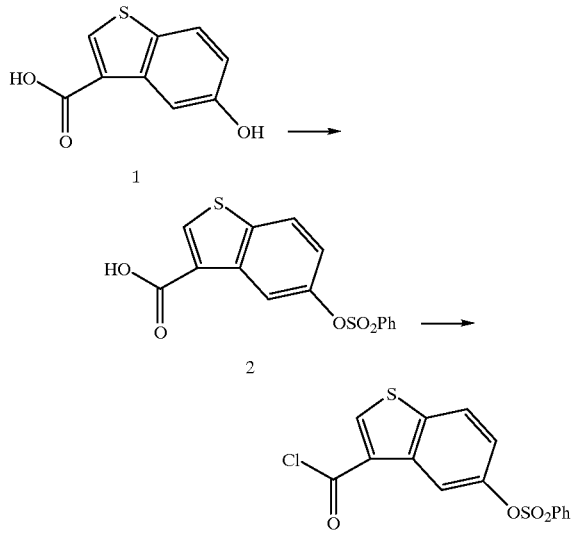

To a solution of 8.63 g (44.4 mmol) of 5-hydroxybenzo [b]thiophene-3-carboxylic acid (1) (J. Chem. Soc (C), 1899–1905 (1967), M. Martin-Smith et al.) in 160 ml of 80% aqueous tetrahydrofuran and 44 ml of 1N sodium hydroxide were added dropwised 87 ml of 0.56N sodium hydroxide and 6.2 ml (48.4 mmol) of benzenesulfonylchloride simultaneously with keeping at pH 11–12 and stirring under ice-cooling. After the reaction, the mixture was diluted with water, alkalized and washed with toluene. The aqueous layer was weakly acidified with conc. hydrochloric acid under stirring. The precipitated crystals were filtered, washed with water and dried to give 14.33 g of 5-benzenesulfonyloxybenzo[b]thiophene-3-carboxylic acid (2).

mp 202–203° C.

NMR δ (CDCl$_3$), 300 MHz 7.16 (1H, dd, J=2.7 and 9.0 Hz), 7.55–7.61 (2H, m), 7.73 (1H, m), 7.81 (1H, d, J=9.0 Hz), 7.90–7.94 (2H, m), 8.16 (1H, d, J=2.7 Hz), 8.60 (1H, s).

IR(Nujol): 3102, 2925, 2854, 2744, 2640, 2577, 1672, 1599, 1558, 1500, 1460, 1451 cm$^{-1}$ Elemental analysis (for C$_{15}$H$_{10}$O$_5$S$_2$). Calcd. (%): C, 53.88; H, 3.01; S, 19.18. Found (%): C, 53.83; H, 3.03; S, 19.04.

A mixture of 5.582 g (16.7 mmol) of the above obtained 5-benzenesulfonyloxybenzo[b]thiophene-3-carboxylic acid (2), a drop of dimethylformamide, 3.57 ml (50 mmol) of thionyl chloride and 22 ml of toluene was refluxed for 1.5 hours and then concentrated under reduced pressure to give 5.89 g of the objective compound (3).

REFERENCE 2

Preparation of 5-Acetoxybenzo[b]thiophene-3-carbonyl Chloride (5)

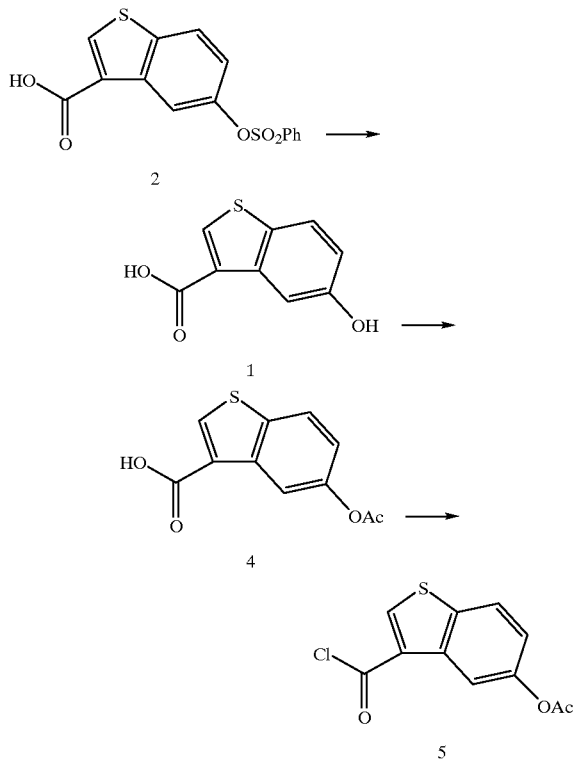

A solution of 100 mg (0.3 mmol) of the above obtained 5-benzenesulfonyloxybenzo[b]thiophene-3-carboxylic acid (2) in 1.2 ml of 1N sodium hydroxide was stirred at 40° C. for 8 hours. Hydrochloric acid (1N, 1.2 ml) was added thereto and the precipitated crystals were filtered, washed with water and dried to give 58 mg of 5-hydroxybenzo[b]thiophene-3-carboxylic acid (1). Yield 96.6%.

mp 262–263° C.

A solution of 1,140 mg of the above obtained 5-hydroxybenzo[b]thiophene-3-carboxylic acid (1) in 2 ml of acetic anhydride and 4 ml of pyridine was allowed to stand for 3 hours. After addition of water, the mixture was stirred for 1.5 hours under ice-cooling and the precipitated crystals were filtered, washed with water and dried to give 1,349 mg of 5-acetoxybenzo[b]thiophene-3-carboxylic acid (4). Yield 97.3%.

mp 239–240° C.

A mixture of 1,349 mg of the above obtained 5-acetoxybenzo[b]thiophene-3-carboxylic acid (4), a drop of dimethylformamide, 1.22 ml of (17.13 mmol) of thionyl chloride and 25 ml of toluene was refluxed for 1.5 hours and then concentrated under reduced pressure to give 1,454 mg of the objective compound (5).

REFERENCE 3

Preparation of (1R, 2S, 3S, 5S)-2-(2-Amino-6,6-dimethylbicyclo[3.1.1]hept-3-yl)ethanol (IVA-b-1) and (1R, 2R, 3S, 5S)-2-(2-Amino-6,6-dimethylbicyclo[3.1.1]hept-3-yl)ethanol (IVA-c-1)

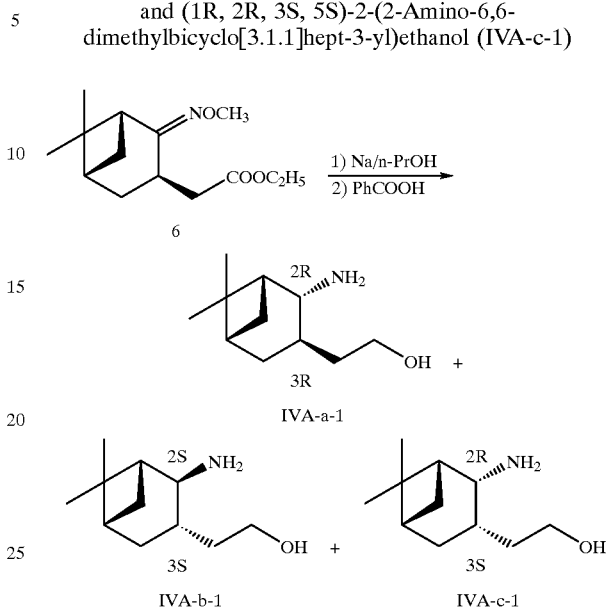

The compound (6) (Chem. Pharm. Bull. Vol. 37, No. 6 1524–1533 (1989)) was reduced with sodium according to the method described in the above literature and the compound (IVA-a-1) was removed by filtration as the benzoic acid salt. The mother liquor (79 g) was suspended in 150 ml of ethyl acetate, adding 260 ml of 1N-hydrochloric acid and the mixture was stirred. The separated aqueous layer was basified with 65 ml of 4N-sodium hydroxide and extracted with ethyl acetate. The organic layer was washed with water, dried over anhydrous magnesium sulfate and concentrated under reduced pressure. Of the obtained oily residue (30 g), 6.7 g was dissolved in 40 ml of 90% methanol, adsorbed to 500 ml of an ion-exchange resin, Amberlite CG-50 ($NH_4^+$) type I and eluted with 2.2 L of water and 1N 2.2 L of aqueous ammonia by a gradient method.

One fraction: 300 ml. Each fraction was checked by thin-layer chromatography (the developing solvent; chloroform:methanol:conc. aqueous ammonia=90:10:1). The fractions 3–8 were collected and concentrated under reduced pressure. The residue was crystallized from hexane; recrystallization afforded 538 mg of needles.

mp 117–118° C.

NMR δ ($CDCl_3$), 300 MHz 1.01 and 1.21 (each 3H, each s), 1.34 (1H, d, J=9.9 Hz), 1.52–1.66 (2H, m), 1.90–2.07 (4H, m), 2.18 (1H, m), 2.48 (1H, m), 3.12 (3H, bs), 3.49 (1H, dd, J=3.9 and 9.6 Hz), 3.61 (1H, dt, J=2.4 and 10.5 Hz), 3.84 (1H, ddd, J=3.3, 4.8 and 10.5 Hz).

IR(Nujol): 3391, 3293, 3108, 2989, 2923, 2869, 2784, 2722, 2521, 1601, 1489, 1466 $cm^{-1}$ $[\alpha]_D^{23}$ −2.5° (c=1.02, $CH_3OH$)

Elemental analysis for ($C_{11}H_{21}NO$). Calcd.: (%): C, 72.08; H, 11.55; N, 7.64. Found: (%): C, 72.04; H, 11.58; N, 7.58.

By means of X-ray crystal analysis, the obtained compound was identified as (1R, 2R, 3S, 5S)-2-(2-amino-6,6-dimethylbicyclo[3.1.1]hept-3-yl)ethanol (IVA-c-1). The mother liquor (2.9 g) after the recrystallization from hexane was dissolved in 15 ml of ethyl acetate, to which was added a solution of 30 ml of ethyl acetate containing 1.93 g of benzoic acid. The precipitated crystals were filtered to give 2.93 g of the benzoic acid salt of the compound (IVA-a-1).

mp 182–183° C.

The fractions 10–17 were collected and concentrated under reduced pressure. To a solution of 2.66 g of the residue in 15 ml of ethyl acetate was added 11 ml of ethyl acetate containing 1.77 g of benzoic acid. The precipitated crystals were filtered to give 4.08 g of needles.

mp 160–161° C.

NMR δ (CDCl$_3$), 300 MHz 0.61 and 1.06 (each 3H, each s), 1.36 (1H, m), 1.53–1.65 (2H, m), 1.75–1.88 (2H, m), 1.95–2.04 (4H, m), 3.18 (1H, d, J=6.3 Hz), 3.58 (1H, dt, J=3.0 and 10.8 Hz), 3.81 (1H, m), 5.65 (4H, bs), 7.33–7.42 (3H, m), 7.98–8.01 (2H, m).

IR(Nujol): 3320, 2922, 2854, 2140, 1628, 1589, 1739, 1459, 1389 cm$^{-1}$ $[\alpha]_D^{23}$ −31.8° (c=1.01, CH$_3$OH)

Elemental analysis (for C$_{18}$H$_{27}$NO$_3$). Calcd.: (%): C, 70.79; H, 8.91; N, 4.59. Found: (%): C, 70.63; H, 8.86; N, 4.58.

By means of X-ray crystal analysis, the structural formula was identified as that of (1R, 2S, 3S, 5S)-2-(2-amino-6,6-dimethylbicyclo[3.1.1]hept-3-yl)ethanol (IVA-b-1).

EXAMPLE 1

Preparation of Sodium (5Z)-7-{(1R,2R,3S,5S)-2-(5-hydroxybenzo[b]thiophen-3-yl-carbonylamino)-6,6-dimethylbicyclo[3.1.1]hept-3-yl}-5-heptenoate (IA-a-6)

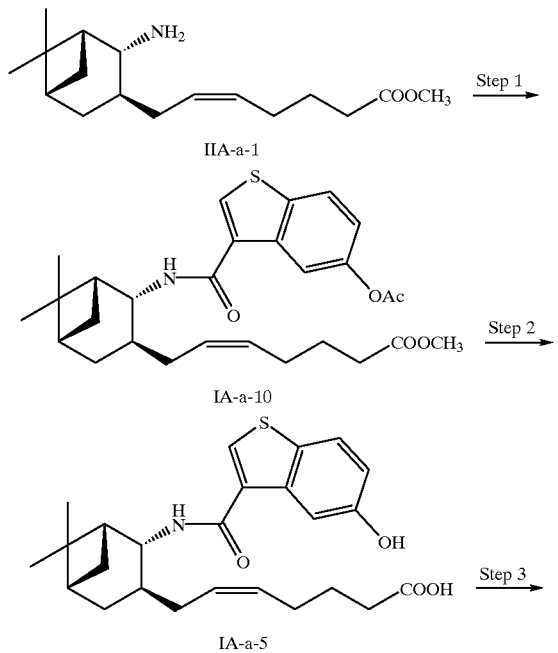

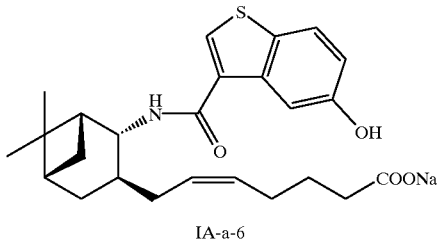

IA-a-6

(Step 1)

To a solution of 1,450 mg (5.2 mmol) of the compound (IIA-a-1) (Japanese Patent Publication (Kokoku) No. 23170/1994) in 25 ml of tetrahydrofuran were added 2.6 ml (18.7 mmol) of triethylamine and 1,454 mg (1.1 mmol) of 5-acetoxybenzo[b]thiophene-3-carbonyl chloride (5) obtained in Reference 2. After stirring for 1.5 hours, the mixture was diluted with water and extracted with toluene. The organic layer was washed with dilute hydrochloric acid and water, dried over anhydrous magnesium sulfate and concentrated under reduced pressure. The residue was chromatographed on silica gel (toluene:ethyl acetate=9:1) to give 2,481 mg of the compound (IA-a-10). Yield 96.1%.

$[\alpha]_D^{23}$=+48.0° (c=1.01%, CH$_3$OH)

Elementary Analysis (for C$_{28}$H$_{35}$NO$_5$S.0.1H$_2$O). Calcd. (%): C, 67.34; H, 7.10; N, 2.80; S, 6.42. Found (%): C, 67.23; H, 7.12; N, 2.86; S, 6.59.

(Step 2)

To a solution of 2,357 mg (4.73 mmol) of the above obtained compound (IA-a-10) in 25 ml of methanol was added 4.1 ml (16.4 mmol) of 4N sodium hydroxide. After stirring for 6 hours, the mixture was neutralized with 17 ml of 1N hydrochloric acid, diluted with water and extracted with ethyl acetate. The organic layer was washed with water, dried over magnesium sulfate and concentrated under reduced pressure. The residue was recrystallized from ethyl acetate/n-hexane to give 1,859 mg of the compound (IA-a-5) as prisms. Yield 86.5%.

mp 142–143° C.

$[\alpha]_D^{23}$=+47.6° (c=1.01%, CH$_3$OH)

Elementary Analysis (for C$_{25}$H$_{31}$NO$_4$S). Calcd. (%): C, 68.00; H, 7.08; N, 3.17; S, 7.26. Found (%): C, 67.93; H, 7.08; N, 3.19; S, 7.24.

(Step 3)

To a solution of 203 mg (0.46 mmol) of the above obtained compound (IA-a-5) in 3 ml of methanol was added 0.42 ml (0.42 mmol) of 1N sodium hydroxide and the mixture was concentrated under reduced pressure. The residue was dissolved in a small quantity of ethyl acetate and diluted with n-hexane. The insolube material was dissolved in methanol and concentrated under reduced pressure to give 210 mg of the objective compound (IA-a-6). Yield 98.5%.

$[\alpha]_D^{25}$=+38.9° (c=1.00%, CH$_3$OH)

Elementary Analysis (for C$_{25}$H$_{30}$NO$_4$SNa.0.5H$_2$O). Calcd. (%): C, 63.54; H, 6.61; N, 2.96; S, 6.78; Na, 4.86. Found (%): C, 63.40; H, 6.69; N, 3.13; S, 6.73; N a, 4.68.

EXAMPLE 2

Preparation of (5Z)-7-[(1R,2S,3R,5S)-2-(5-hydroxybenzo[b]thiophen-3-yl-carbonylamino)-6,6-dimethyl-bicyclo[3.1.1]hept-3-yl]-5-heptenoic Acid (IA-b-1)

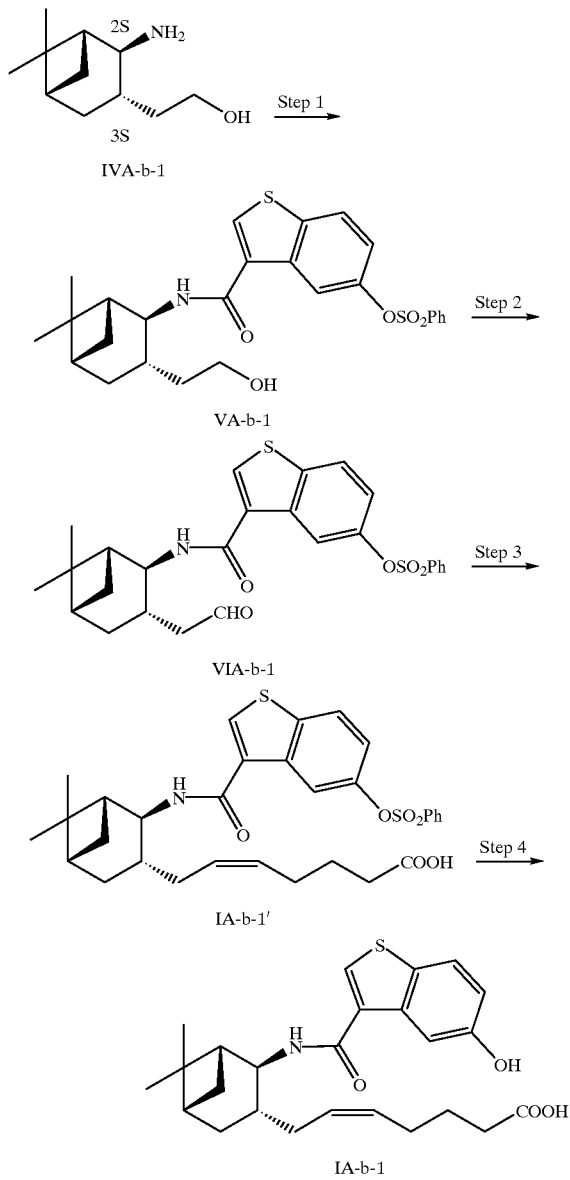

(Step 1)

To a suspension of 916 mg (3 mmol) of (1R, 2S, 3S, 5S)-2-(2-amino-6,6-dimethylbicyclo[3.1.1]hept-3-yl) ethanol benzoic acid salt in 3 ml of water was added 3.1 ml of 1N hydrochloric acid. The precipitated benzoic acid was extracted with ethyl acetate. The aqueous layer was adjusted to pH 10.5 with 700 mg of anhydrous sodium carbonate, to which was dropwise added a solution of 1.06 g (3 mmol) of 5-benzenesulfonyloxybenzo[b]thiophene-3-carbonyl chloride (3) in 6 ml of tetrahydrofuran. After 1.5 hours, the mixture was diluted with water and extracted with toluene. The organic layer was washed with water, dried over anhydrous magnesium sulfate and concentrated under reduced pressure. The residue (1.5 g) was chromatographed on silica gel (hexane:ethyl acetate=1:1) to give 1.497 g of the compound (VA-b-1). Yield 99.8%.

$[\alpha]_D^{23}$ –31.1° (c=1.00, $CH_3OH$)

Elemental analysis (for $C_{26}H_{29}NO_5S_2.0.2H_2O$). Calcd. (%): C, 62.05; H, 5.89; N, 2.78; S, 12.74. Found (%): C, 62.03; H, 5.93; N, 2.79; S, 12.72.

(Step 2)

A solution of 0.61 ml (8.6 mmol) of dimethylsulfoxide in 9.7 ml of 1,2-dimethoxyethane was cooled to –60° C., to which was dropwise added 0.37 ml (4.3 mmol) of oxalyl chloride. After 15 minutes, a solution of 1.427 g (2.9 mmol) of the above obtained compound (VA-b-1) in 11 ml of 1,2-dimethoxyethane was added thereto at the some temperature. After stirring for 30 minutes, 1.2 ml of triethylamine was added and the mixture was stirred for 30 minutes to gradually rise to room temperature. The mixture was diluted with water and extracted with toluene. The organic layer was washed with water, dried over anhydrous magnesium sulfate and concentrated under reduced pressure. The residue was chromatographed on silica gel (hexane:ethyl acetate=6:4) to give 1.338 g of the compound (VIA-b-1). Yield 94.1%.

$[\alpha]_D^{24}$ –29.1° (c=1.01, $CH_3OH$)

Elemental analysis (for $C_{26}H_{27}NO_5S_2.0.4H_2O$). Calcd. (%): C, 61.85; H, 5.55; N, 2.77; S, 12.70. Found (%): C, 61.92; H, 5.60; N, 2.79; S, 12.88.

(Step 3)

A suspension of 1.72 g (3.9 mmol) of 4-carboxybutyltriphenylphosphonium bromide and 1.016 g (9 mmol) of potassium t-butoxide in 9 ml of tetrahydrofuran was stirred for 1 hour under ice-cooling. To the mixture was added a solution of 1.288 g (2.6 mmol) of the above obtained compound (VIA-b-1) in 4 ml of tetrahydrofuran over 6 minutes and the mixture was stirred at the same temperature for 2 hours. The mixture was diluted with 15 ml of water, acidified to pH 10.5 with 1N hydrochloric acid and washed with 15 ml of toluene twice. The aqueous layer was adjusted with 1N hydrochloric acid to pH 8.0, followed by adding 1.15 g (10.4 mmol) of anhydrous calcium chloride and the mixture was extracted with 15 ml of ethyl acetate twice. The organic layer was diluted with 16 ml of water, acidified with 1N hydrochloric acid to pH 2–3 and extracted with ethyl acetate. The organic layer was washed with water, dried over anhydrous magnesium sulfate and concentrated under reduced pressure to give 1.44 g of the compound (IA-b-1'). Yield 95.5%. The compound was used for the next step without further purification.

(Step 4)

To a solution of 1.44 g (2.6 mmol) of the above obtained compound (IA-b-1') in 2.8 ml of dimethylsulfoxide was added 3.9 ml of 4N sodium hydroxide and the mixture was stirred at 55° C. for 3 hours. The mixture was diluted with water and washed with 15 ml of toluene twice. The aqueous layer was acidified with 1N hydrochloric acid and extracted with ethyl acetate. The organic layer was washed with water, dried over anhydrous magnesium sulfate and concentrated under reduced pressure to give 1.097 g of the compound (IA-b-1). Yield 95.9%.

$[\alpha]_D^{25}$ –43.0° (c=1.01, $CH_3OH$)

Elemental analysis (for $C_{25}H_{31}NO_4S.0.2H_2O$). Calcd. (%): C, 67.45; H, 7.11; N, 3.15; S, 7.20. Found (%): C, 67.51; H, 7.15; N, 3.38; S, 6.96.

EXAMPLE 3

Preparation of (5E)-7-[(1R,2R,3S,5S)-2-(5-hydroxybenzo[b]thiophen-3-yl-carbonylamino)-6,6-dimethylbicyclo[3.1.1]hept-3-yl]-5-heptenoic Acid (IA-a-17)

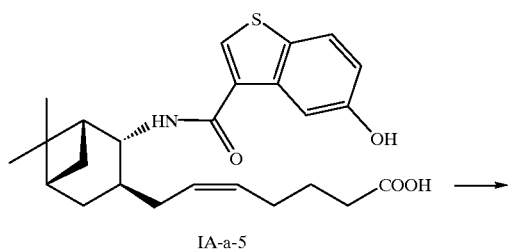

IA-a-5

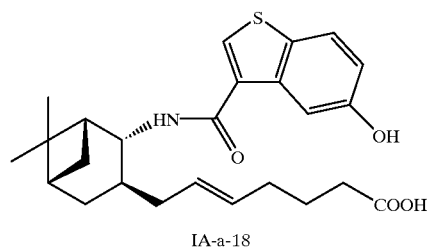

IA-a-18

A solution of 11.04 g (25 mmol) of (5Z)-7-[(1R,2R,3S,5S)-2-(5-hydroxybenzo[b]thiophen-3-yl-carbonylamino)-6,6-dimethylbicyclo[3.1.1]hept-3-yl]-5-heptenoic acid (IA-a-5), 4.32 g (18.8 mmol) of 1-methyltetrazol-5-yl disulfide (J. Org. Chem., 50, 2794–2796 (1985), M. Narisada, Y. Terui, M. Yamakawa, F. Watanebe, M. Ohtani and H. Miyazaki et al.) and 2.84 g (17.3 mmol) of 2,2'-azobisisobutyronitrile in 1.1 L of benzene was refluxed with stirring for 8 hours. The mixture was extracted with 400 ml of 0.4 N sodium hydroxide twice. The aqueous layer was acidified with hydrochloric acid and the precipitate was collected by filtration. The precipitate (11.08 g) was chromatographed on silica gel (chloroform:methanol=10:1). The obtained compound (6.93 g) was dissolved in 69 ml of dimethoxyethane, to which was added 2.15 g of 4-methoxybenzylamine and successively diluted with 120 ml of ether under ice-cooling. The precipitate was filtered to give 7.45 g of a crystalline product, which was recrystallized from isopropyl alcohol/ethyl acetate/ether (=2/10/5) for purification.

mp 108–111° C.

$[\alpha]_D^{23}$+18.9° (c=1.00, CH$_3$OH)

The purity of the isomer of the above-obtained 4-methoxybenzyamine salt was analyzed by HPLC. Result: (E-isomer):(Z-isomer)=98.4:1.6. [HPLC condition] Column: YMC-pack AM-303–10(10 μm.120A.ODS) (4.6 mm Φ×250 mm); flow rate: 1 ml/min; detection: UV 254 nm; mobile phase: acetic acid/water/acetonitrile=0.1/52/48; retention time: (E-isomer) 21 minutes, (Z-isomer) 23 minutes.

The purified 4-methoxybenzylamine salt (1.6 g) was suspended in 25 ml of water, acidified with 25 ml of hydrochloric acid and extracted with ethyl acetate. The organic layer was washed with water, dried over anhydrous magnesium sulfate and concentrated under reduced pressure to give 1.21 g of the compound (IA-a-17).

$[\alpha]_D^{24}$+14.4° (c=1.01, CH$_3$OH)

Elemental analysis (for C$_{25}$H$_{31}$NO$_4$S·0.1H$_2$O) Calcd. (%): C, 67.72; H, 7.09; N, 3.16; S, 7.23. Found (%): C, 67.59; H, 7.26; N, 3.35; S, 7.39.

Compounds and physical constants obtained in the same manner as the above Examples are shown in the following table 1-table 14.

TABLE 1

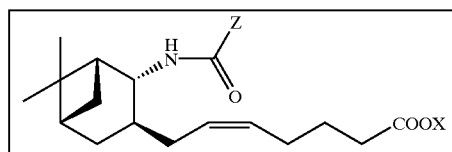

| Compd. No. | X | Z |
|---|---|---|
| IA-a-1 | H | 3-methyl-4-bromobenzo[b]thiophene |
| IA-a-2 | H | 3-methyl-5-bromobenzo[b]thiophene |
| IA-a-3 | H | 3-methyl-6-bromobenzo[b]thiophene |
| IA-a-4 | H | 3-methyl-7-bromobenzo[b]thiophene |
| IA-a-5 | H | 3-methyl-5-hydroxybenzo[b]thiophene |
| IA-a-6 | Na | 3-methyl-5-hydroxybenzo[b]thiophene |
| IA-a-7 | H | 3-methyl-6-hydroxybenzo[b]thiophene |
| IA-a-8 | H | 3-methyl-7-hydroxybenzo[b]thiophene |

TABLE 1-continued
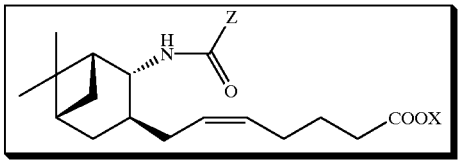
| Compd. No. | X | Z |
|---|---|---|
| IA-a-9 | H | 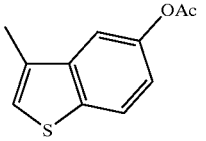 |
| IA-a-10 | CH₃ | 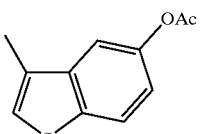 |
| IA-a-11 | H | 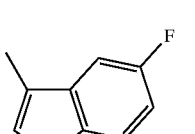 |
| IA-a-12 | H | 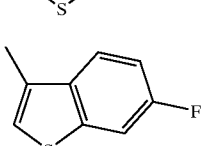 |
| IA-a-13 | H | 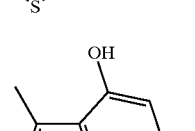 |
| IA-a-14 | H | 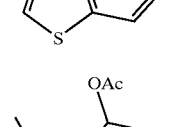 |
| IA-a-15 | H | 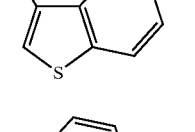 |
| IA-a-16 | H | 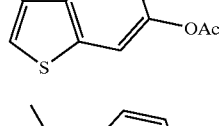 |
| IA-a-17 | H | 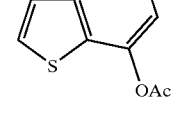 |
TABLE 2
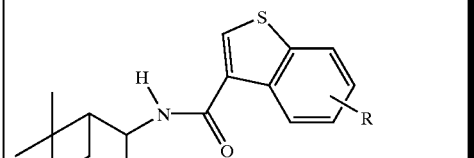
| Compd. No. | |
|---|---|
| IA-a-18 | 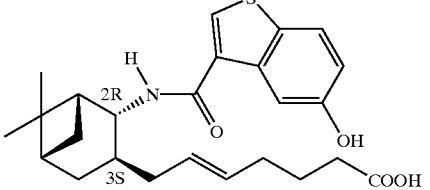 |
| IA-c-1 | 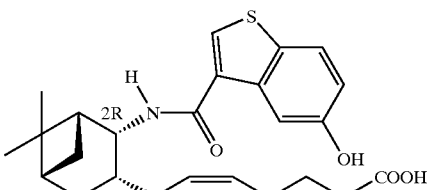 |
| IA-c-2 | 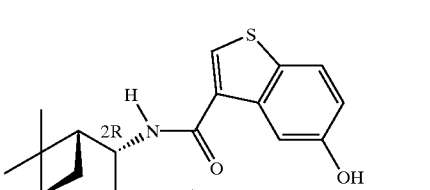 |
| IA-c-3 | 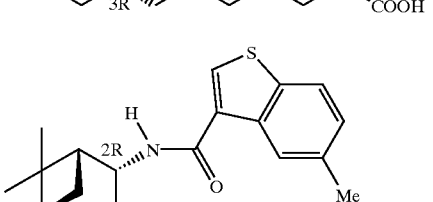 |
| IA-c-4 | 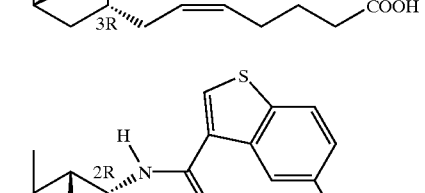 |
| IA-b-1 | 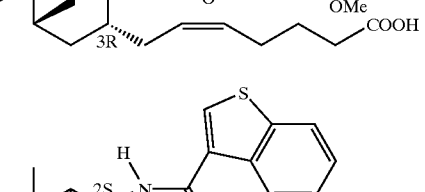 |

TABLE 2-continued
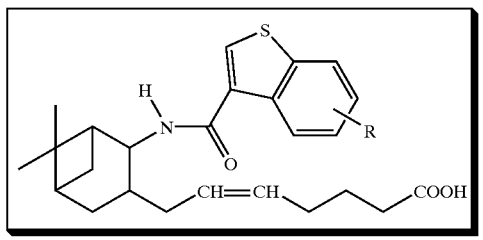
Compd. No.
IA-b-2
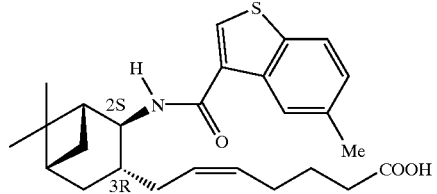
IA-b-3
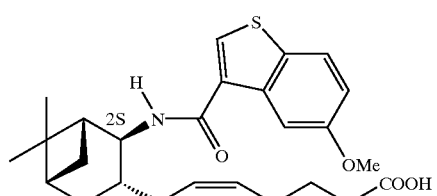
IA-d-1
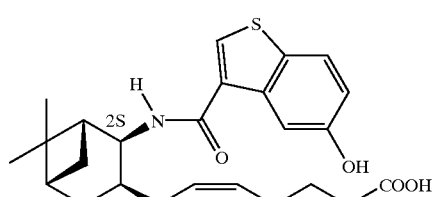
IA-d-2
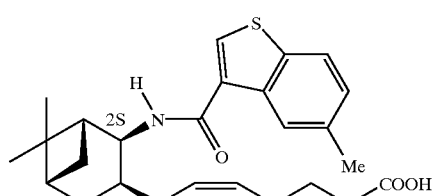
IA-d-3
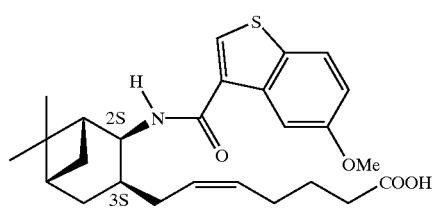
IA-b'-1
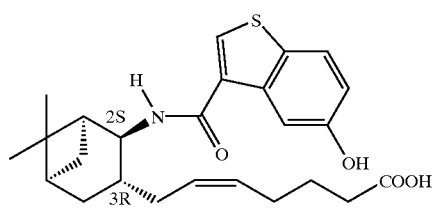
TABLE 2-continued
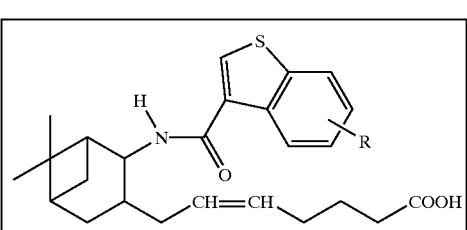
Compd. No.
IA-b'-2
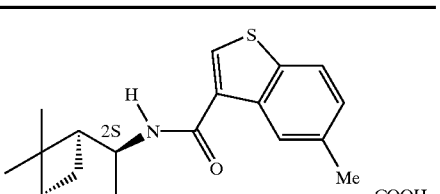
IA-b'-3
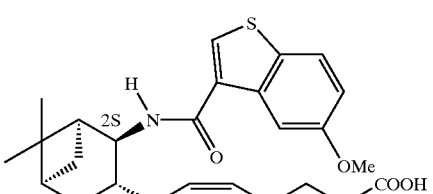
TABLE 3
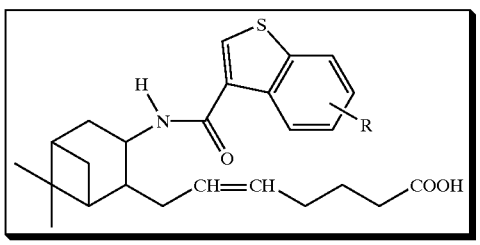
Compd. No.
IB-b'-1
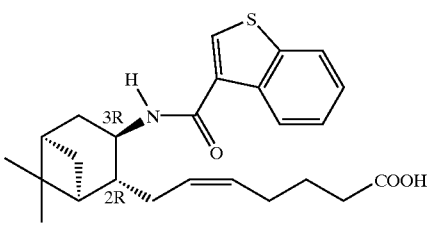
IB-b'-2
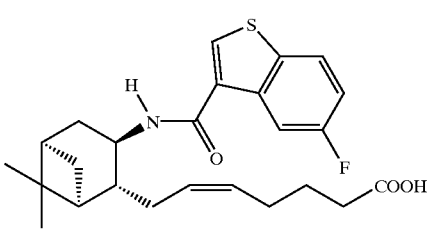

TABLE 3-continued
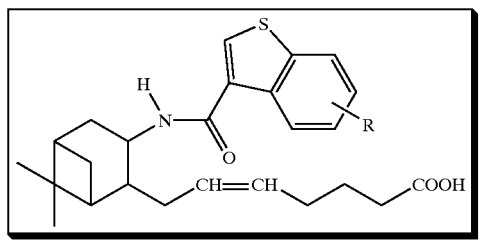
Compd. No.
IB-b'-3
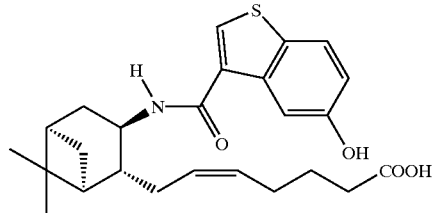
IB-a'-1
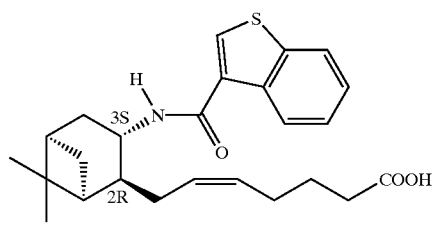
IB-a'-2
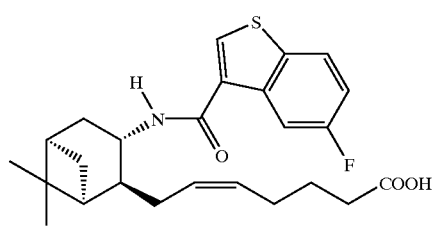
IB-a'-3
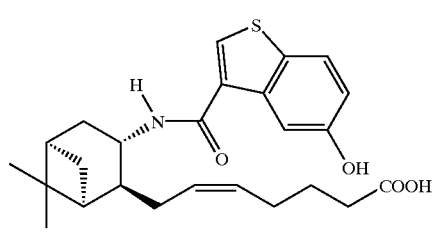
IB-b'-4
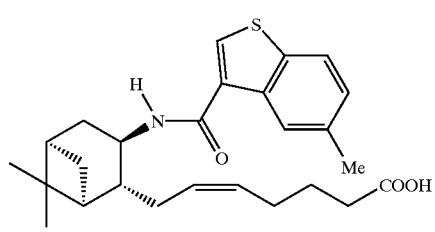
TABLE 3-continued
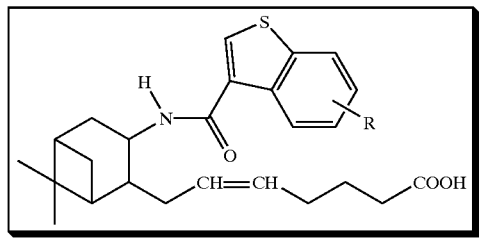
Compd. No.
IB-b'-5
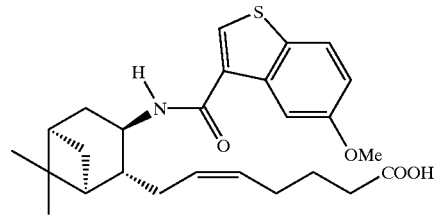
IB-a'-4
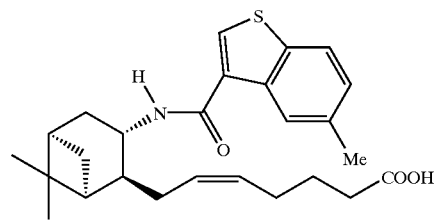
IB-a'-5
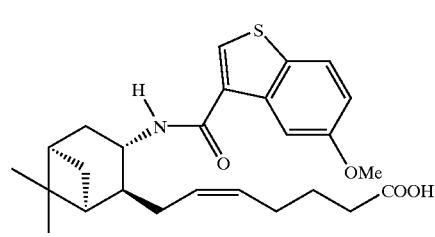
TABLE 4
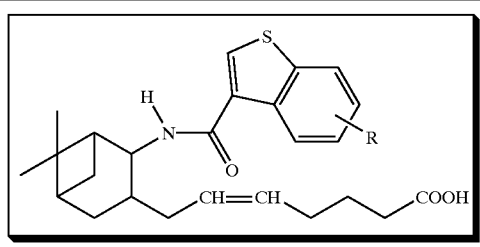
Compd. No.
IA-a'-1
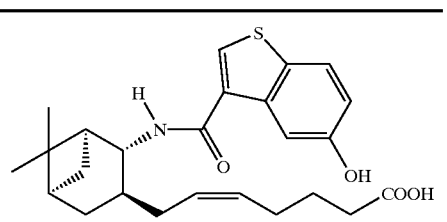

TABLE 4-continued
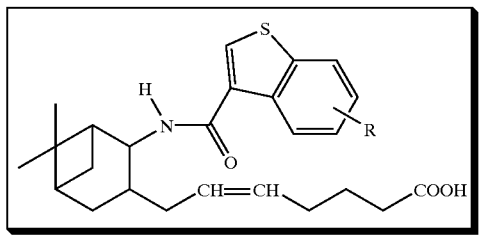
Compd. No.
IA-a'-2
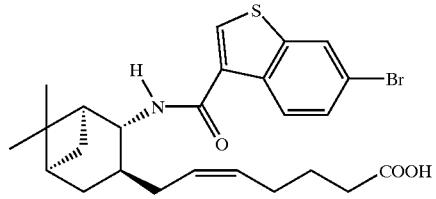
IA-a'-3
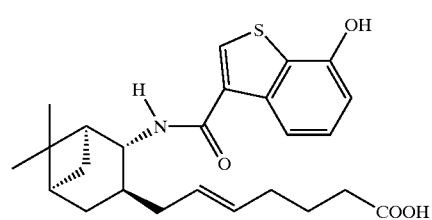
IA-c'-1
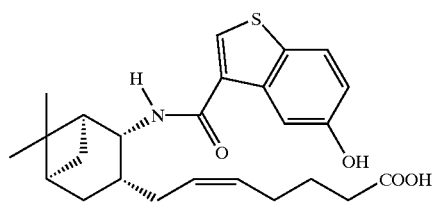
IA-c'-2
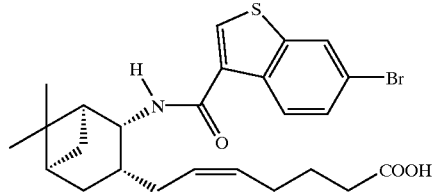
IA-c'-3
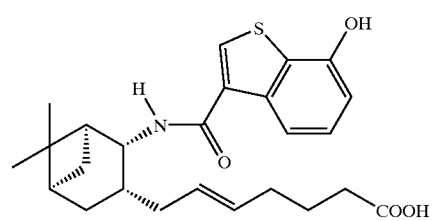
IA-a'-4
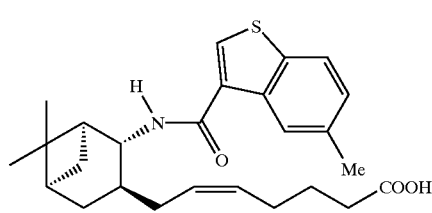
TABLE 4-continued
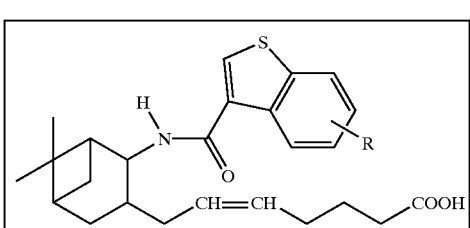
Compd. No.
IA-a'-5
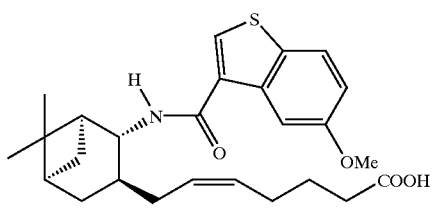
IA-c'-4
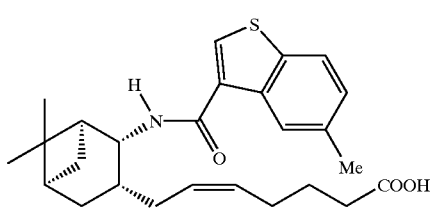
IA-c'-5
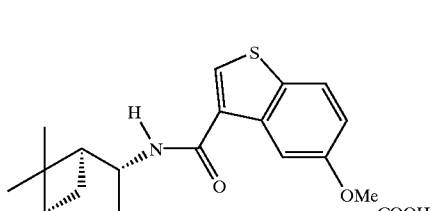
TABLE 5
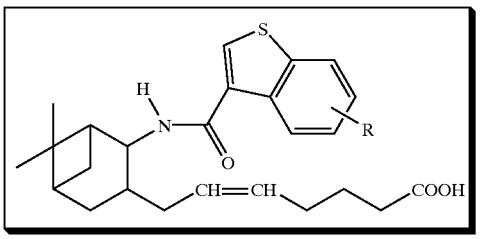
Compd. No.
IA-d'-1
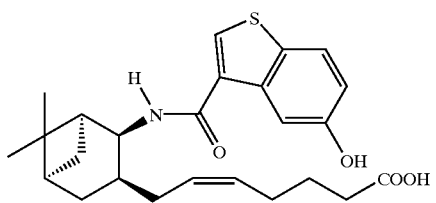

TABLE 5-continued

| Compd. No. | Structure |
|---|---|
| IA-d'-2 | 6-Br substituted benzothiophene carboxamide pinane derivative with CH=CH-CH2-COOH chain |
| IA-d'-3 | 7-OH substituted benzothiophene carboxamide pinane derivative |
| IA-d'-4 | 5-Me substituted benzothiophene carboxamide pinane derivative |
| IA-d'-5 | 5-OMe substituted benzothiophene carboxamide pinane derivative |

TABLE 6

| Compd. No. | Structure |
|---|---|
| IB-a-1 | Benzothiophene-3-carboxamide pinane derivative |
| IB-a-2 | 5-F substituted benzothiophene carboxamide pinane derivative |
| IB-a-3 | 5-OH substituted benzothiophene carboxamide pinane derivative |
| IB-b-1 | Benzothiophene-3-carboxamide pinane derivative (b-series) |
| IB-b-2 | 5-F substituted benzothiophene carboxamide pinane derivative (b-series) |

TABLE 6-continued
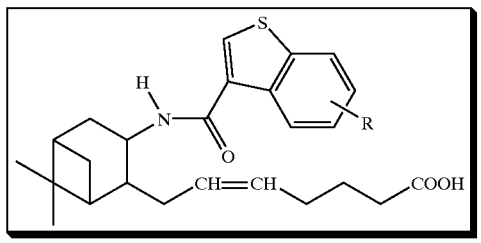
Compd. No.
IB-b-3
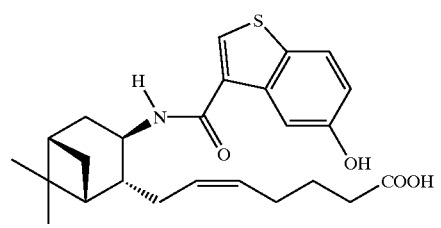
IB-a-4
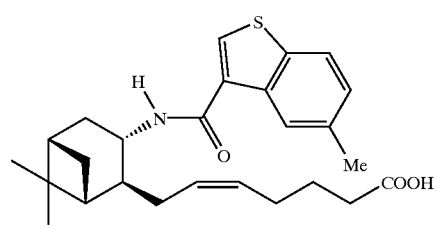
IB-a-5
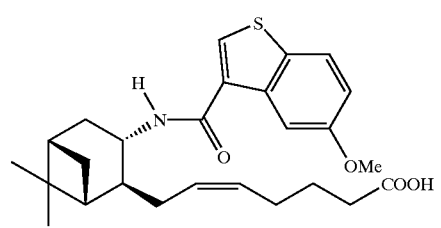
IB-b-4
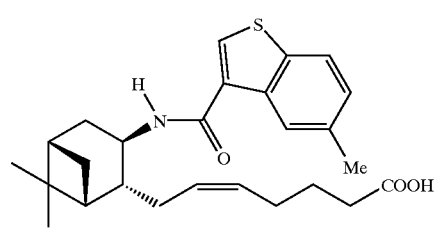
IB-b-5
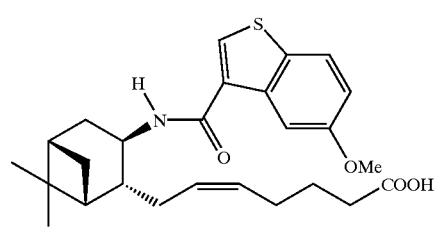
TABLE 7
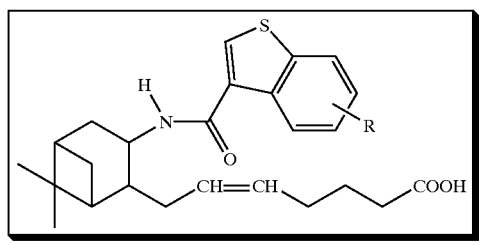
Compd. No.
IB-c-1
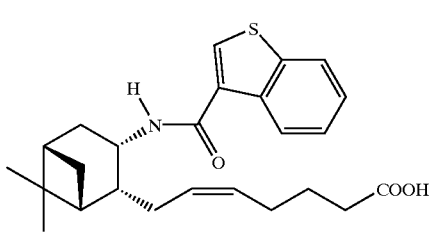
IB-c-2
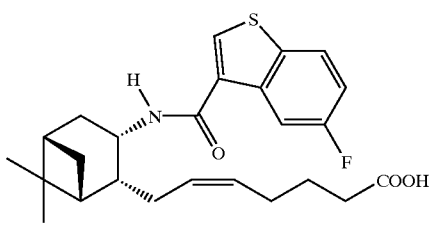
IB-c-3
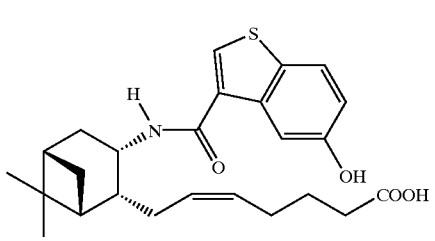
IB-d-1
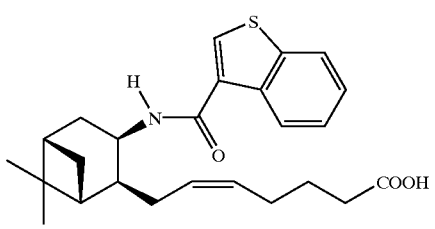
IB-d-2
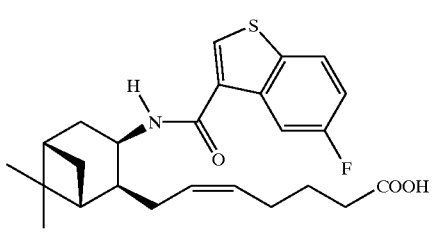

TABLE 7-continued
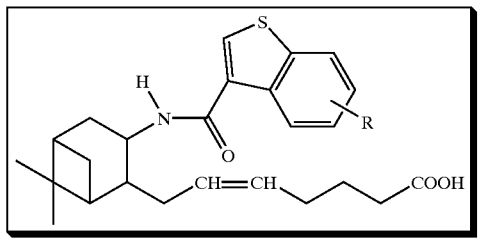
Compd. No.
IB-d-3
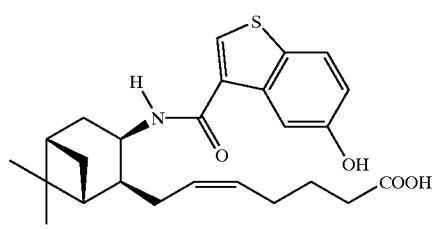
IB-c-4
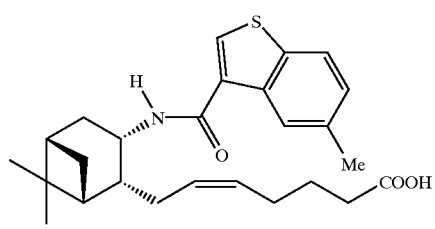
IB-c-5
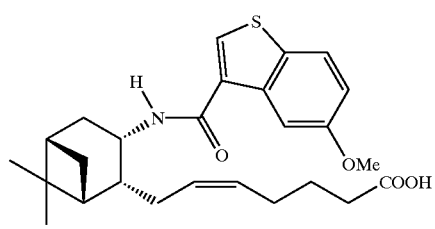
IB-d-4
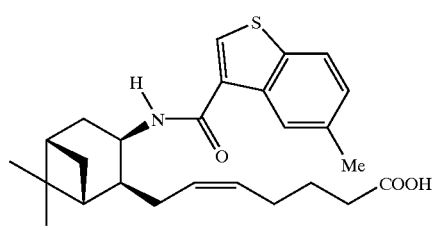
IB-d-5
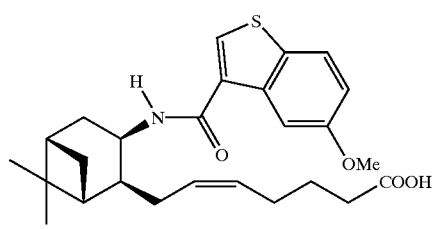
TABLE 8
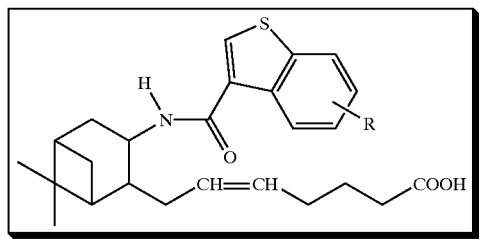
Compd. No.
IB-c'-1
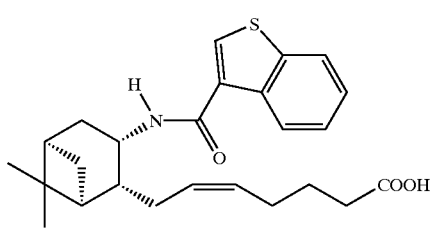
IB-c'-2
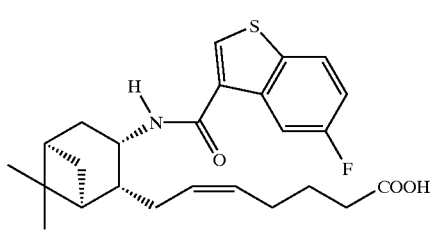
IB-c'-3
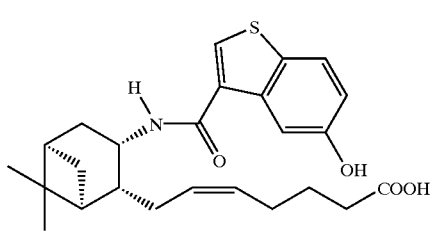
IB-d'-1
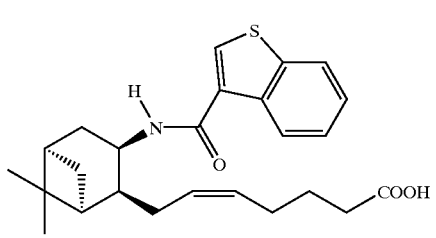
IB-d'-2
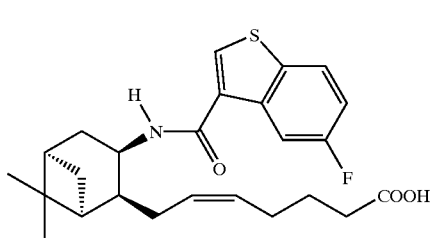

TABLE 8-continued

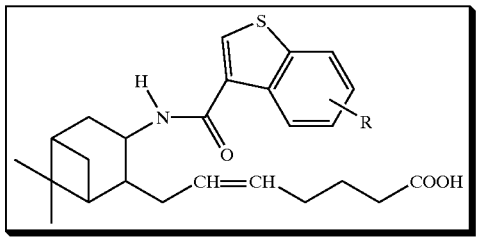

| Compd. No. | |
|---|---|
| IB-d'-3 | ![structure with OH] |
| IB-c'-4 | ![structure with Me] |
| IB-c'-5 | ![structure with OMe] |
| IB-d'-4 | ![structure with Me] |
| IB-d'-5 | ![structure with OMe] |

TABLE 9

| Compd. No | Physical property |
|---|---|
| IA-a-1 | NMR δ (CDCl$_3$ ppm), 300MHz<br>0.97(1H, d, J=10.2Hz), 1.16 and 1.25(each 3H, each s), 1.53–2.46(14H, m), 4.28(1H, m), 5.36–5.53(2H, m), 6.34 (1H, d, J=8.7Hz), 7.26(1H, t, 7.8Hz), 7.56(1H, dd, J=0.9 and 7.8Hz), 7.77(1H, m), 7.80(1H, d, J=0.6Hz).<br>IR(CHCl$_3$): 3509, 3446, 3429, 1738, 1708, 1651, 1548, 1525, 1498 cm$^{-1}$. [α]D +53.4°(CH$_3$OH, c=1.01, 25° C.). |
| IA-a-2 | 0.99(1H, d, J=10.2Hz), 1.13 and 1.26(each 3H, each, s), 1.54–2.51(14H, m), 4.32(1H, m), 5.37–5.54(2H, m), 6.17 (1H, d, J=8.4Hz), 7.49(1H, dd, J=1.8 and 8.7Hz), 7.72 (1H, d, J=8.7Hz), 7.81(1H, s), 8.54(1H, d, J=1.8Hz).<br>IR(CHCl$_3$): 3517, 3443, 2665, 1708, 1654, 1514 cm$^{-1}$. [α]D +39.5°(CH$_3$OH, c=1.00, 26° C.). |
| IA-a-3 | 0.98(1H, d, J=10.2Hz), 1.11 and 1.24(each 3H, each s), 1.53–2.50(14H, m), 4.32(1H, m), 5.36–5.54(2H, m), 6.18 (1H, d, J=8.7Hz), 7.54(1H, dd, J=1.8 and 8.7Hz), 7.75 (1H, s), 7.98(1H, d, J=7.5Hz), 8.23(1H, d, J=8.7Hz).<br>IR(CHCl$_3$): 3517, 3443, 3095, 1708, 1654, 1585, 1512 cm$^{-1}$. [α]D +49.4°(CH$_3$OH, c=1.01, 23° C.). |
| IA-a-4 | 0.99(1H, d, J=10.2Hz), 1.12 and 1.25(each 3H, each s), 1.54–2.51(14H, m), 4.32(1H, m), 5.36–5.54(2H, m), 6.19 (1H, d, J=9.0Hz), 7.34(1H, dd, J=7.8 and 8.4Hz), 7.55 (1H, m), 7.86(1H, s), 8.33(1H, dd, J=0.9 and 8.4Hz).<br>IR(CHCl$_3$): 3517, 3442, 3095, 2667, 1708, 1653, 1545, 1515 cm$^{-1}$. [α]D +54.6°(CH$_3$OH, c=1.01, 23° C.). |

TABLE 10

| Compd. No. | Physical property |
|---|---|
| IA-a-5 | 1.02(1H, d, J=10.2Hz), 1.12 and 1.24(each 3H, each s), 1.56–2.55(14H, m), 4.29(1H, m), 5.32–5.51(2H, m), 6.20(1H, d, J=9.3Hz), 7.01(1H, dd, J=2.4 and 9.0Hz), 7.66 (1H, d, J=9.0Hz), 7.69(1H, s), 8.03(1H, d, J=2.4Hz).<br>IR(CHCl$_3$): 3600, 3440, 3226, 1707, 1638, 1602, 1516 cm$^{-1}$.<br>[α]D +47.6°(CH$_3$OH, c=1.00, 23°). mp 142–143° C. |
| IA-a-6 | (CD$_3$OD)0.97(1H, d, J=9.9Hz), 1.16 and 1.25(each 3H, each s), 1.55–2.43(14H, m), 4.18(1H, m), 5.41–5.53 (2H, m), 6.93(1H, dd, 0.6 and 8.7Hz), 7.68(1H, dd, 0.6 and 8.7Hz), 7.71(1H, m), 8.01(1H, s).<br>IR(KBr): 3436, 2621, 1637, 1600, 1557, 1520, 1434 cm$^{-1}$.<br>[α]D +38.9°(CH$_3$OH, c=1.00, 25° C.). |
| IA-a-7 | 0.97(1H, d, J=10.2Hz), 1.10 and 1.23(each 3H, each s), 1.54–2.52(14H, m), 4.32(1H, m), 5.35–5.54(2H, m), 6.26 (1H, d, J=8.7Hz), 6.98(1H, dd, J=2.4 and 9.0Hz), 7–26 (1H, m), 7.58(1H, s), 8.07(1H, d, J=9.0Hz).<br>IR(CHCl$_3$): 3592, 3439, 3223, 3102, 1708, 1639, 1604, 1518 cm$^{-1}$.<br>[α]D +51.5°(CH$_3$CH, c=1.01, 25° C.). |
| IA-a-8 | 0.96(1H, d, J=10.2Hz), 1.11 and 1.24(each 3H, each s), 1.54–2.53(14H, m), 4.34(1H, m), 5.35–5.53(2H, m), 6.31 (1H, d, J=9.0Hz), 6.79(1H, d, J=7.5Hz), 7.25(1H, dd, J=7.5 and 8.4Hz), 7.74(1H, d, J=8.4Hz), 7.86(1H, s).<br>IR(CHCl$_3$): 3586, 3437, 3104, 1708, 1638, 1568, 1522, 1501, 1471 cm$^{-1}$. [α]D +57.1°(CH$_3$CH, c=1.01, 25° C.). |

TABLE 11

| Compd. No. | Physical property |
|---|---|
| IA-a-9 | 0.98(1H, d, J=10.2Hz), 1.12 and 1.25(each 3H, each s); 1.54–2.51(14H, m), 2.33(3H, s), 4.30(1H, m), 5.36–5.54(2H, m), 6.17(1H, d, J=8.7Hz), 7.15(1H, dd, J=2.1 and 9.0Hz), 7.83 (1H, d, J=9.0Hz), 7.84(1H, s), 8.11(1H, d, J=2.1Hz).<br>IR(CHCl$_3$): 3510, 3443, 2665, 1758, 1708, 1653, 1514 cm$^{-1}$.<br>[α]D +47.8°(CH$_3$OH, c=1.00, 25° C.). |
| IA-a-17 | NMR δ(CDCl$_3$), 300MHz<br>1.00(1H, d, J=10.5Hz), 1.12 and 1.23(each 3H, each s), 1.50– |

TABLE 11-continued

| Compd. No. | Physical property |
|---|---|
| | 1.66(3H, m), 1.84–2.03(4H, m), 2.17–2.40(7H, m), 4.33(1H, m), 5.42–5.45(2H, m), 6.16(1H, d, J=9.0Hz), 7.01(1H, dd, J=2.4 and 8.7Hz), 7.66(1H, d, J=8.7Hz), 7.69(1H, s), 8.04(1H, d, J=2.4Hz). IR(CHCl$_3$): 3441, 3237, 3035, 3009, 2992, 2924, 2870, 1708, 1637, 1601, 1516, 1436 cm$^{-1}$ [α]$_D^{24}$ +14.4°(c=1.01%, CH$_3$OH) |
| IA-c-1 | 1.09 and 1.25(each 3H, each s), 1.50(1H, d, J=9.9Hz), 1.52–1.69(3H, m), 2.02–2.30(10H, m), 2.49(1H, m), 4.89(1H, dt, J=3.9 and 9.6Hz), 5.30–5.54(2H, m), 6.49(1H, d, J=9.6Hz), 7.03(1H, dd, J=2.4 and 8.7Hz), 7.67(1H, d, J=8.7Hz), 7.74(1H, s), 8.00(1H, d, J=2.4Hz). IR(CHCl$_3$): 3464, 3225, 3022, 3016, 2924, 2870, 1707, 1639, 1602, 1519, 1479, 1459, 1437 cm$^{-1}$ [α]$_D^{25}$ −57.1°(c=1.00%, CH$_3$OH) |

TABLE 12

| Compd. No. | Physical property |
|---|---|
| IA-c-2 | 1.08 and 1.25(each and each s), 1.49–1.62(4H, m), 1.84–2.10(5H, m), 2.14–2.30(5H, m), 2.56(1H, m), 4.89(1H, dt, J=3.3 and 9.9Hz), 5.25–5.40(2H, m), 6.50(1H, d, J=10.2Hz), 7.04(1H, dd, J=2.4 and 9.0Hz), 7.68(1H, d, J=9.0Hz), 7.69(1H, s), 8.09(1H, d, J=2.4Hz). IR(Nujol): 3460, 3178, 2927, 2854, 2726, 2680, 1702, 1639, 1600, 1517 cm$^{-1}$ [α]$_D^{24}$ −34.6°(c=1.01%, CH$_3$OH) mp 166–167° C. |
| IA-b-1 | 1.00 and 1.23(each and each s), 1.22–1.40(6H, m), 1.92–2.25(8H, m), 2.47(1H, m), 4.32(1H, t, J=8.6Hz), 5.26–5.50(2H, m), 6.15(1H, d, J=9.0Hz), 7.02(1H, dd, J=2.4 and 8.7Hz), 7.65(1H, d, J=8.7Hz), 7.73(1H, s), 8.07(1H, d, J=2.4Hz). IR(CHCl$_3$): 3423, 3223, 3033, 3016, 2925, 2870, 1707, 1638, 1601, 1436 cm$^{-1}$ [α]$_D^{25}$ −43.0°(c=1.01%, CH$_3$OH) |
| IA-d-1 | 1.06 and 1.23(each and each s), 1.07(1H, d, J=9.9Hz), 1.51–1.68(3H, m), 1.80–2.60(11H, m), 4.81(1H, dt, J=2.7 and 9.9 Hz), 5.29–5.51(2H, m), 6.32(1H, d, J=9.6Hz), 7.02(1H, dd, J=2.4 and 9.0Hz), 7.66(1H, d, J=9.0Hz), 7.77(1H, s), 7.99(1H, d, J=2.4Hz). IR(CHCl$_3$): 3394, 3163, 2926, 2854, 2681, 2609, 1698, 1636, 1599, 1529, 1458, 1437 cm$^{-1}$ [α]$_D^{25}$ +77.3°(c=1.01%, CH$_3$OH) mp 148–149° C. |

TABLE 13

| Compd. No. | Physical property |
|---|---|
| IA-b'-1 | 1.02(1H, d, J=10.2Hz), 1.13 and 1.24(each 3H, each s), 1.56–2.55(14H, m), 4.29(1H, m), 5.35–5.51(2H, m), 6.20(1H, d, J=9.3Hz), 7.01(1H, dd, J=2.4 and 9.0Hz), 7.65(1H, d, J=9.0Hz), 7.69(1H, s), 8.00(1H, d, J=2.4Hz) IR(CHCl$_3$): 3440, 3226, 1708, 1637, 1602, 1516 cm$^{-1}$ [α]$_D^{25}$ −49.9°(c=1.01%, CH$_3$OH) mp 143–144° C. |
| IB-b'-1 | 0.87 and 1.24(each 3H, each s), 1.51(1H, d, J=10.5Hz), 1.60–2.61(14H, m), 4.24(1H, m), 5.32–5.45(2H, m), 6.12(1H, d, J=9.0Hz), 7.37–7.48(2H, m), 7.85–7.88(2H, m), 8.33(1H, d, J=7.8Hz) IR(CHCl$_3$): 3429, 3067, 3023, 3014, 2923, 2871, 1708, 1652, 1556, 1516, 1494 cm$^{-1}$ [α]$_D^{25}$ −23.0°(c=1.00%, CH$_3$OH) |
| IB-b'-2 | 1.11 and 1.24(each 3H, each s), 1.50(1H, d, J=10.8Hz), 1.59–2.60(14H, m), 4.2(1H, m), 5.32–5.45(2H, m), 6.09(1H, d, J=8.4Hz), 7.16(1H, ddd, J=2.4, 9.0 and 10.2Hz), 7.77(1H, dd, J=4.8 and 9.0Hz), 7.93(1H, s), 8.09(1H, dd, J=2.4 and 0.2Hz) IR(CHCl$_3$): 3429, 3095, 3030, 3015, 2923, 2871, 1708, 1653, 1603, 1566, 1517, 1432 cm$^{-1}$ [α]$_D^{25}$ −22.4°(c=1.01%, CH$_3$OH) |
| IB-b'-3 | 0.86 and 1.23(each 3H, each s), 1.49–2.58(15H, m), 4.24(1H, m), 5.25–5.40(2H, m), 6.18(1H, d, J=9.0Hz), 7.03(1H, dd, |

TABLE 13-continued

| Compd. No. | Physical property |
|---|---|
| | J=2.4 and 8.7Hz), 7.66(1H, d, J=8.7Hz), 7.77(1H, s), 8.06(1H, d, J=2.4Hz). IR(CHCl$_3$): 3425, 3237, 3029, 3021, 3017, 2924, 2871, 1707, 1637, 1519, 1457, 1437 cm$^{-1}$ [α]$_D^{25}$ −18.7°(c=1.00%, CH$_3$OH) |

TABLE 14

| Compd. No. | Physical property |
|---|---|
| IB-a'-1 | 0.91(1H, d, J=10.2Hz), 1.13 and 1.25(each 3H, each s), 1.60–1.88(3H, m), 2.01–2.50(10H, m), 2.79(1H, t, J=11.6Hz), 4.54(1H, m), 5.31–5.50(2H, m), 6.10(1H, d, J=8.4Hz), 7.37–7.48(2H, m), 7.85–7.88(2H, m), 8.33(1H, d, J=7.5Hz). IR(CHCl$_3$): 3429, 3065, 3023, 3015, 2923, 2872, 1708, 1651, 1556, 1516, 1493 cm$^{-1}$ [α]$_D^{25}$ +26.5°(c=1.01%, CH$_3$OH) |
| IB-a'-2 | 0.91(1H, d, J=10.2Hz), 1.12 and 1.25(each 3H, each s), 1.60–1.90(3H, m), 2.01–2.50(10 H, m), 2.78(1H, t, J=12.2Hz), 4.52(1H, m), 5.30–5.50(2H, m), 6.08(1H, d, J=8.4Hz), 7.16(1H, dt, J=2.7 and 8.7Hz), 7.77(1H, dd, J=4.5 and 8.7Hz), 7.91(1H, s), 8.09(1H, dd, J=2.7 and 9.9Hz). IR(CHCl$_3$): 3430, 3095, 3024, 3015, 2923, 2872, 1708, 1652, 1603, 1565, 1517, 1433 cm$^{-1}$ [α]$_D^{25}$ +25.8°(c=1.00%, CH$_3$OH) |
| IB-a'-3 | 0.88(1H, d, J=9.9Hz), 1.11 and 1.26(each 3H, each s), 1.50–1.90(3H, m), 2.00–2.23(8H, m), 2.40–2.50(2H, m), 2.83(1H, t, J=12.0Hz), 4.55(1H, m), 5.24–5.44(2H, m), 6.11(1H, d, J=9.0Hz), 7.02(1H, dd, J=2.4 and 8.4Hz), 7.67(1H, d, J=8.4Hz), 7.75(1H, s), 8.12(1H, d, J=2.4Hz). IR(CHCl$_3$): 3425, 3222, 3028, 3022, 3015, 2923, 2872, 1707, 1637, 1601, 1519, 1456, 1437 cm$^{-1}$ [α]$_D^{25}$ +19.3°(c=1.00%, CH$_3$OH) |

The compounds prepared in Examples above were tested as shown in Experimental examples below.

EXPERIMENT 1

Binding to PGD$_2$ Receptor

Materials and Methods (1) Preparation of Human Platelet Membrane Fraction

Blood sample was obtained using a plastic syringe containing 3.8% sodium citrate from the vein of healthy volunteers (adult male and female), put into a plastic test tube and mixed gently by rotation. The sample was then centrifuged at 1800 rpm, 10 min at room temperature and the supernatant containing PRP (platelet-rich plasma) was collected. The PRP was re-centrifuged at 2300 rpm, 22 min at room temperature to obtain platelets. The platelets mere homogenized using a homogenizer (Ultra-Turrax) followed by centrifugation 3 times at 20,000 rpm, 10 min at 4° C. to obtain a platelet membrane fraction. After protein determination, the membrane fraction was adjusted to 2 mg/ml and preserved in a refrigerator at −80° C. until use.

(2) Binding to PGD$_2$ Receptor

To a binding-reaction solution (50 mM Tris/HCl, pH 7.4, 5 mM MgCl$_2$) (0.2 ml) were added the human platelet membrane fraction (0.1 mg) and 5 nM [$^3$H]PGD$_2$ (115 Ci/mmol). After reacting at 4° C. for 90 min, the mixture was filtered through a glass fiber filter paper and washed several times with cooled saline, to measure the radioactivity retained on the filter paper. The specific binding was calculated by subtracting the non-specific binding (the binding in the presence of 10 μM PGD$_2$) from the total binding.

The inhibitory activity of each compound was expressed as the concentration required for 50% inhibition ($IC_{50}$), which was determined by depicting a substitution curve by plotting the binding ratio (%) in the presence of each compound, where the binding ratio in the absence of a test compound is 100%. The results are shown in Table 15.

TABLE 15

| Compound No. | $IC_{50}$ (nM) |
|---|---|
| IA-a-2 | 3.3 |
| IA-a-5 | 0.4 |
| IA-a-7 | 1.3 |
| IA-a-9 | 6.5 |
| IA-a-11 | 0.27 |
| IA-a-17 | 32 |
| IA-a-18 | 1.2 |
| IA-c-1 | 28 |
| IA-c-2 | 1 |
| IB-a'-2 | 37 |

EXPERIMENT 2

Investigation on Itch-Related Scratching Behavior in Mouse Pruritus Model: Effect on Compound 48/80-Induced Scratching Behavior Compound 48/80 (10 μg/site, Sigma), a non-immunological mast cell activator, was dissolved in physiological saline and subcutaneously injected into the rostral part of the back of female C57BL mice (8–12 weeks of age, Charles River Japan Inc.). After the injection, scratching behavior was observed for 30 minutes. Mice usually scratched several times successively in one behavior and a series of scratching was counted as one incidence.

Compound Treatment

Compound (IA-a-5), suspended in 0.5% methylcellulose, was orally administered 1 hour before the injection of compound 48/80 at a dose of 300 mg/kg. As a control, mice were treated with 0.5% methlycellulose. Results were shown in Table 16. *: P<0.05 versus control (Wilcoxon test).

TABLE 16

| | Mean ± S.E.(Number of scratching) |
|---|---|
| Control (n = 10) | 122.2 ± 12.7 |
| Compd. (IA-a-5) 300 mg/kg (n = 10) | 81.8 ± 17.9* |

(Wilcoxon test, P < 0.05)

EXPERIMENT 3

Investigation on Itch-Related Scratching Behavior in Mouse Pruritus Model: Effect on Antigen-Induced Scratching Behavior 50 μl of diluted anti-benzylpenicilloyl (BPO) IgE monoclonal antibody was intradermally injected to the rostral part of the back skin of female C57BL (Table 17, 8–12 weeks of age, Charles River Japan Inc.) or male DS-Nh (Table 18, 7–8 weeks of age, Aburahi Laboratories, Shionogi & Co., Ltd.) mice. Twenty-four hours later, scratching behavior was induced by intravenously injection of physiological saline containing 1 mg of BPO-guinea pig serum albumin. Scratching behavior was observed for 15 minutes (Table 17) or 10 minutes (Table 18) as described above.

In Table 17, the compound was treated in the same manner described in above 1). In Table 18, the compound were dissolved in physiological saline and intraperitoneally injected 30 minutes before antigen challenge. *: P<0.05, **: P<0.01 versus control (Dunnett's test).

TABLE 17

| | Mean ± S.E. (Number of scratching) |
|---|---|
| Control (n =7) | 51.6 ± 5.3 |
| Compd. (IA-a-5) 100 mg/kg (n = 7) | 48.4 ± 12.4 |
| Compd. (IA-a-5) 300 mg/kg (n = 7) | 19.6 ± 6.5* |

(Dunnett's test, P < 0.05)

TABLE 18

| | Mean ± S.E. (Number of scratching) |
|---|---|
| Control (n =5) | 47.8 ± 8.0 |
| Compd. (IA-a-17) Na salt 100 mg/kg (n = 5) | 11.6 ± 3.0** |
| Compd. (IA-a-11) Na salt 100 mg/kg (n = 5) | 4.4 ± 1.9** |
| Compd. (IA-a-7) Na salt 100 mg/kg (n = 5) | 29.2 ± 11.6 |
| Control (n = 6) | 52.3 ± 7.2 |
| Compd. (IA-a-11) Na salt 10 mg/kg (n = 6) | 43.7 ± 6.2 |
| Compd. (IA-a-11) Na salt 30 mg/kg (n = 6) | 40.0 ± 5.4 |
| Compd. (IA-a-11) Na salt 100 mg/kg (n = 6) | 18.2 ± 3.3** |

(Dunnett's test, P < 0.01)

As shown in Experiment 2, scratching caused by skin itching derived from the activation of mast cell was reduced in the test group of a compound (IA-a-5) as compared with the control group. As shown Experiment 3, scratching of the test group, caused by skin itching derived from the antigen-stimulation, was reduced as compared with the control group.

As shown above, a compound of the present invention is useful as a pharmaceutical composition for preventing or treating diseases accompanied by itching derived from allergic reaction or the similar reaction thereto, for example, atopic dermatitis, urticaria, atopic conjunctivitis, allergic rhinitis and contact dermatitis. Moreover, the present compound is applicable to a pharmaceutical composition for preventing or treating secondary diseases such as cararacta, retinal separation, inflammation, infection, dysgryphia and the like, caused by an action accompanied by itching, for example, scratching, knocking and the like.

| Formulation example 1 tablet | |
|---|---|
| compound (IA-a-5) | 40.0 mg |
| hydroxypropyl cellulose | 3.6 mg |
| magnesium stearate | 0.4 mg |
| corn starch | 18.0 mg |
| saccharum lactis | 58.0 mg |
| Total | 120.0 mg |
| Formulation example 2 unguentum | |
| compound (IA-a-5) | 0.1 g |
| liquid paraffin | 1.5 g |
| white petrolatum | 18.4 g |
| Total | 20.0 g |

Industrial Applicability

As shown clearly in the above experiments, a compound of the present invention has an activity for the prevention or treatment of itching. Therefore, the compound of the present invention is useful as a pharmaceutical composition for the prevention or treatment of itching and applicable to a pharmaceutical composition for preventing or treating diseases accompanied by itching, for example, atopic dermatitis, urticaria, allergic conjunctivitis, allergic rhinitis, contact dermatitis and the like. Moreover, the present compound is applicable to a pharmaceutical composition for the prevention or treatment of a secondary disease such as cararacta, retinal separation, inflammation, infection, dysgryphia and the like, caused by an action accompanied by itching, for example, scratching, knocking and the like.

What is claimed is:

1. A method of preventing or treating itching caused by PGD$_2$ comprising administering to a patient in need of such treatment a compound of formula (I):

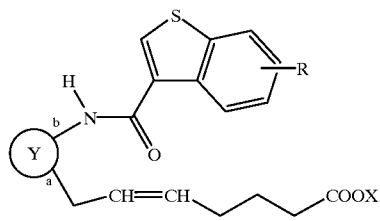

wherein

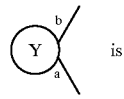

is

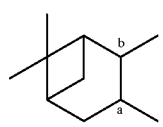

or

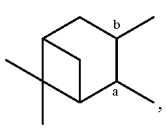

wherein R is hydroxy and X is hydrogen, a pharmaceutically accetable salt thereof or a hydrate thereof.

2. The method of preventing or treating itching caused by PGD$_2$ according to claim 1 comprising administering to a patient in need of such treatment an effective amount of a compound of formula (IA-a-5):

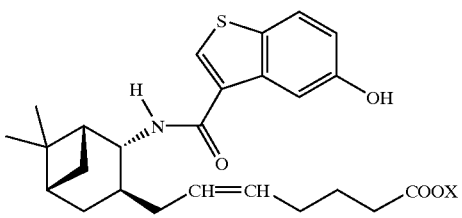

wherein X is as defined as in claim 1 and the double bond on the α chain has E configuration or Z configuration, a pharmaceutically acceptable salt thereof or a hydrate thereof.

3. The method of preventing or treating itching according to claim 1, wherein the itching is caused by an antigen.

4. The method of preventing or treating itching according to claim 1, wherein the itching is derived from atopic dermatitis.

5. The method of preventing or treating itching according to claim 1, wherein the itching is derived from urticaria.

6. The method of preventing or treating itching according to claim 1, wherein the itching is derived from allergic conjuctivitis.

7. The method of preventing or treating itching according to claim 1, wherein the itching is derived from allergic rhinitis.

8. The method of preventing or treating itching according to claim 1, wherein the itching is derived from contact dermatitis.

* * * * *